(12) United States Patent
Mickle et al.

(10) Patent No.: US 12,076,316 B2
(45) Date of Patent: *Sep. 3, 2024

(54) LEVORPHANOL PRODRUGS AND PROCESSES FOR MAKING AND USING THEM

(71) Applicant: ZEVRA THERAPEUTICS, INC., Celebration, FL (US)

(72) Inventors: Travis Mickle, Celebration, FL (US); Sven Guenther, Coralville, IA (US); Sanjib Bera, Blacksburg, VA (US)

(73) Assignee: ZEVRA THERAPEUTICS INC.

( * ) Notice: Subject to any disclaimer, the term of this patent is extended or adjusted under 35 U.S.C. 154(b) by 143 days.

This patent is subject to a terminal disclaimer.

(21) Appl. No.: 17/550,328

(22) Filed: Dec. 14, 2021

(65) Prior Publication Data
US 2022/0096463 A1 Mar. 31, 2022

Related U.S. Application Data

(63) Continuation of application No. 16/604,710, filed as application No. PCT/US2018/027263 on Apr. 12, 2018, now Pat. No. 11,234,975.

(60) Provisional application No. 62/485,890, filed on Apr. 14, 2017, provisional application No. 62/485,891, filed on Apr. 14, 2017.

(51) Int. Cl.
*C07D 221/28* (2006.01)
*A61K 31/439* (2006.01)
*A61K 31/485* (2006.01)
*A61K 47/54* (2017.01)
*A61K 45/06* (2006.01)

(52) U.S. Cl.
CPC .......... *A61K 31/485* (2013.01); *A61K 47/542* (2017.08); *A61K 45/06* (2013.01)

(58) Field of Classification Search
CPC ... C07D 221/28; C07D 221/22; A61K 31/439
USPC .............................................. 546/74; 514/289
See application file for complete search history.

(56) References Cited

U.S. PATENT DOCUMENTS

| 3,766,188 A | 10/1973 | Murakami et al. |
| 8,829,020 B2 | 9/2014 | Cantrell et al. |
| 11,234,975 B2 * | 2/2022 | Mickle .................. C07D 221/28 |

OTHER PUBLICATIONS

Opheim, et al., Stereospecific interaction of quaternized opiate, N-methyllevorphanol, with opiate receptors, J. Med. Chem., vol. 19, pp. 857-858, 1976.
Wainer, et al., Gas phase electron ionization fragmentation of dextromethorphan and related quaternary ammonium salts, Biomed. Mass Spectrometry, vol. 11, pp. 529-534, 1984.

* cited by examiner

*Primary Examiner* — Charanjit Aulakh
(74) *Attorney, Agent, or Firm* — MCANDREWS HELD & MALLOY, LTD

(57) ABSTRACT

The presently described technology provides compositions of one or more of oxoacids, amino acids, polyethylene glycols, and/or vitamin compounds chemically conjugated to levorphanol ((−)-17-methylmorphinan-3-ol) to form novel prodrugs and compositions of levorphanol.

15 Claims, 17 Drawing Sheets

STRUCTURES OF SOME HYDROXYBENZOATES

STRUCTURES OF SOME HETEROARYL CARBOXYLIC ACIDS

STRUCTURES OF SOME PHENYLACETATES

FIGURE 5
STRUCTURES OF SOME BENZYLACETATES
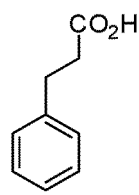
3-phenylpropanoic acid
(benzylacetic acid)
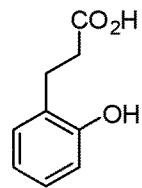
Melilotic acid
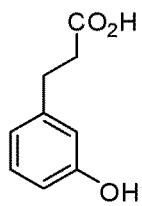
3-hydroxyphenyl-
propanoic acid
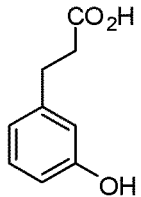
4-hydroxyphenyl-
propanoic acid
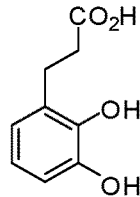
2,3-dihydroxyphenyl-
propanoic acid
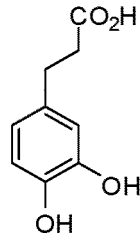
3,4-dihydroxyphenyl-
propanoic acid
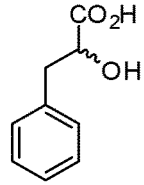
Phenyllactic acid

STRUCTURES OF SOME CINNAMATES

FIGURE 7
STRUCTURES OF SOME DICARBOXYLIC ACIDS

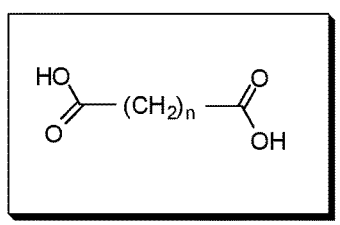

When
- n = 0  Oxalic acid
- n = 1  Malonic acid
- n = 2  Succinic acid
- n = 3  Glutaric acid
- n = 4  Adipic acid
- n = 5  Pimelic acid
- n = 6  Suberic acid
- n = 7  Azelaic acid
- n = 8  Sebacic acid

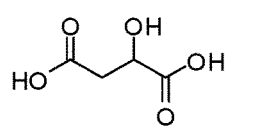 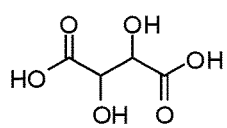 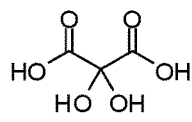 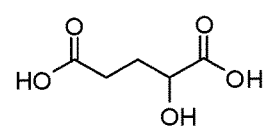

Malic acid  Tartaric acid  dihydroxymesoxalic acid  α-hydroxyglutaric acid

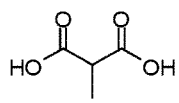 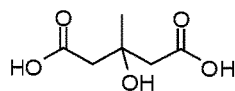 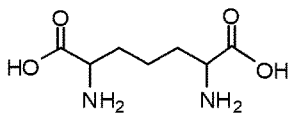 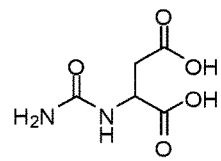

Methylmalonic acid  Meglutol  Diaminopimelic acid  Carbamoyl aspartic acid

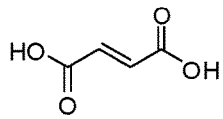 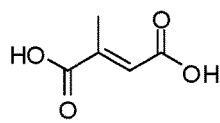 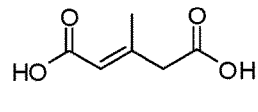

Fumaric acid (trans isomer)  Mesaconic acid  3-methylglutaconic acid
Maleic acid (cis isomer)

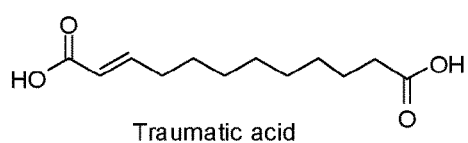

Traumatic acid

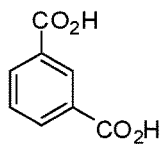 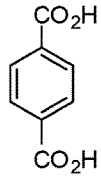 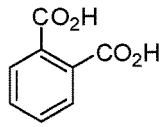 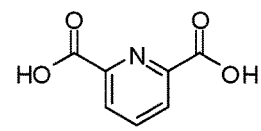

Isophthalic acid  Terephthalic acid  Phthalic acid  Dipicolinic acid

FIGURE 8
STRUCTURES OF SOME TRICARBOXYLIC ACIDS
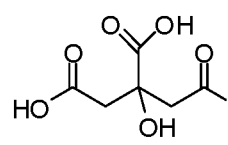 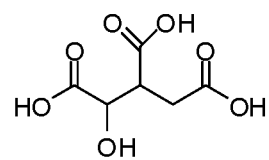 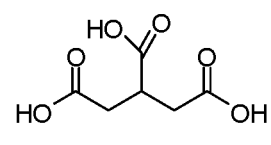 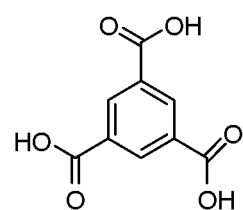
Citric acid　　　　Isocitric acid　　　　Carballyilc acid　　　　Trimesic acid

FIGURE 9
GENERAL STRUCTURES OF THE STANDARD AMINO ACIDS

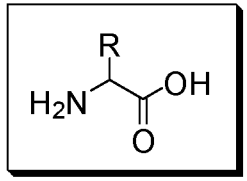

R =

| R group | Amino acid |
|---|---|
| -H | Glycine |
| -CH₃ | Alanine |
| -CH₂-C₆H₅ | Phenylalanine |
| -CH₂-C₆H₄-OH | Tyrosine |
| -CH₂-COOH | Aspartic acid |
| -CH₂CH₂-COOH | Glutamic acid |
| -CH₂-CONH₂ | Asparagine |
| -CH₂CH₂-CONH₂ | Glutamine |
| -(CH₂)₄-NH₂ | Lysine |
| -(CH₂)₃-NH-C(NH)-NH₂ | Arginine |
| -CH₂-SeH | Selenocysteine |
| -CH₂-(imidazole) | Histidine |
| -CH₂-OH | Serine |
| -CH₂-SH | Cysteine |
| -CH(OH)-CH₃ | Threonine |
| -CH₂CH₂-S-CH₃ | Methionine |
| -CH(CH₃)₂ | Valine |
| -CH₂-CH(CH₃)₂ | Leucine |
| -CH(CH₃)-CH₂CH₃ | Isoleucine |
| -CH₂-(indole) | Tryptophan |
| (cyclic, proline) | Proline |
| (pyrrolysine side chain) | Pyrrolysine |

FIGURE 10
STRUCTURES OF SOME NON-STANDARD AMINO ACIDS
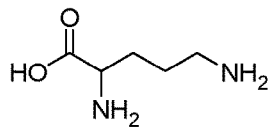
Ornithine
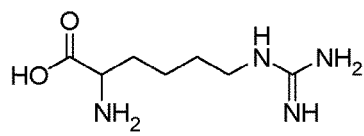
Homoarginine
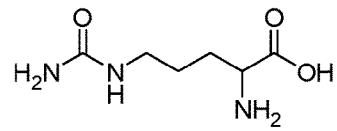
Citrulline
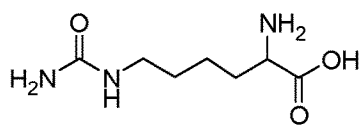
Homocitrulline
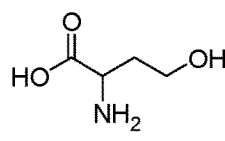
Homoserine
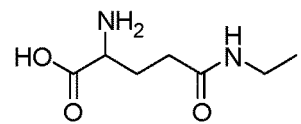
Theanine
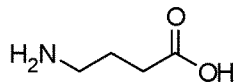
γ-Aminobutyric acid
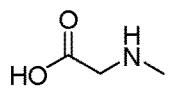
Sarcosine
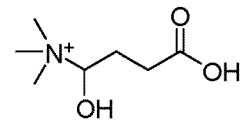
Carnitine
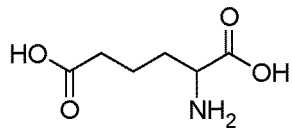
2-Aminoadipic acid
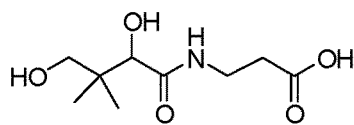
Pantothenic acid
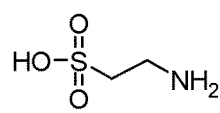
Taurine
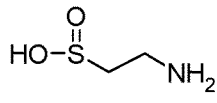
Hypotaurine
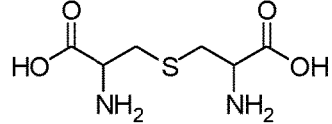
Lanthionine
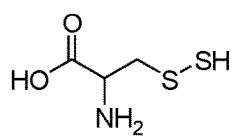
Thiocysteine
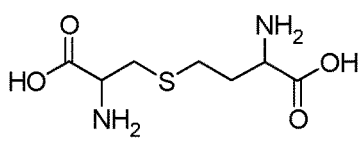
Cystathionine
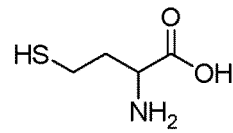
Homocysteine FIGURE 10 (CONT.)
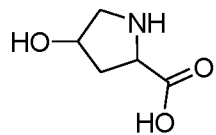
4-Hydroxyproline
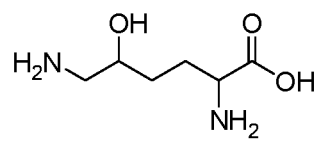
5-Hydroxylysine
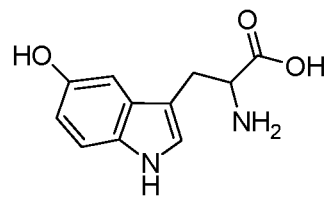
5-Hydroxy-tryptophan
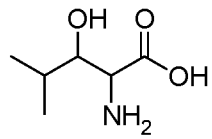
3-Hydroxyleucine
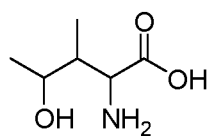
4-Hydroxyisoleucine
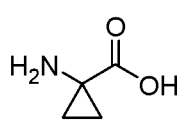
1-Aminocyclopropyl-1-carboxylic acid
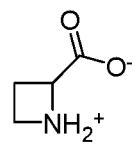
Azetidine-2-carboxylic acid
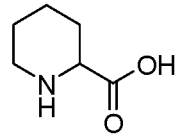
Pipecolic acid

FIGURE 11
STRUCTURES OF SOME SYNTHETIC AMINO ACIDS

Allylglycine

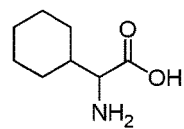
Cyclohexylglycine

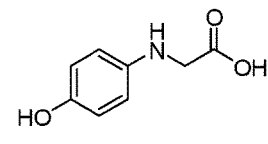
N-(4-Hydroxyphenyl)glycine

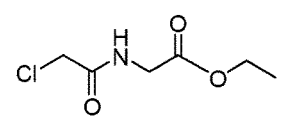
N-(Chloroacetyl)glycine ethyl ester

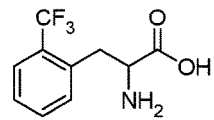
2-(Trifluoromethyl)-phenylalanine

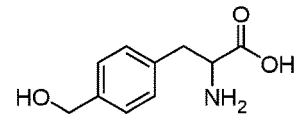
4-(Hydroxymethyl)-phenylalanine

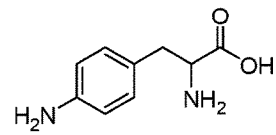
4-Amino-phenylalanine

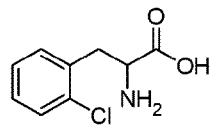
2-Chlorophenylglycine

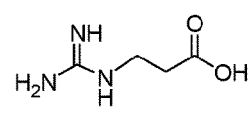
3-Guanidinopropionic acid

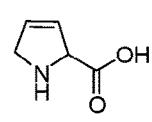
3,4-Dehydro-proline

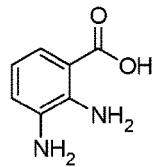
2,3-Diaminobenzoic acid

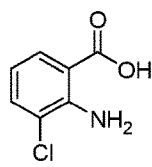
2-Amino-3-chlorobenzoic acid

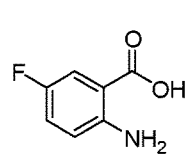
2-Amino-5-fluorobenzoic acid

FIGURE 12A
CHEMICAL STRUCTURES OF WATER SOLUBLE VITAMINS
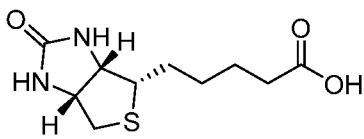
Biotin (Vitamin B₇)
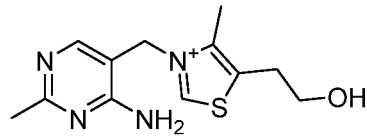
Thiamin (Vitamin B₁)
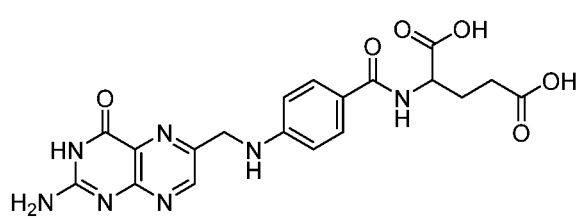
Folic Acid
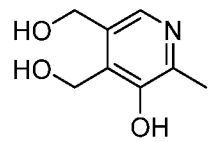
Pyridoxine (Vitamin B₆)
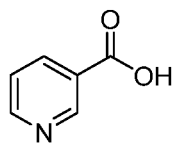
Niacin
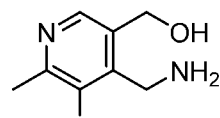
Pyridoxamine (Vitamin B₆)
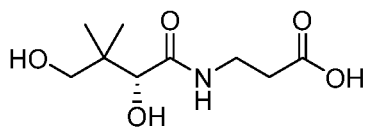
Pantothenic acid (Vitamin B₅)
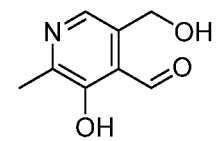
Pyridoxal (Vitamin B₆)
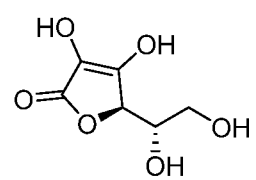
Ascorbic acid (Vitamin C)
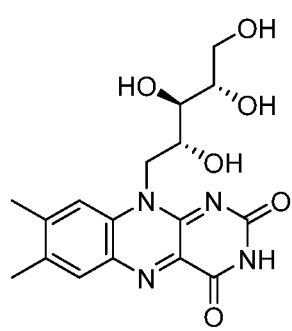
Riboflavin (Vitamin B₂)

FIGURE 12B
CHEMICAL STRUCTURES OF FAT SOLUBLE VITAMINS
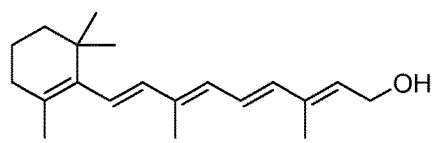
Retinol (Vitamin A)
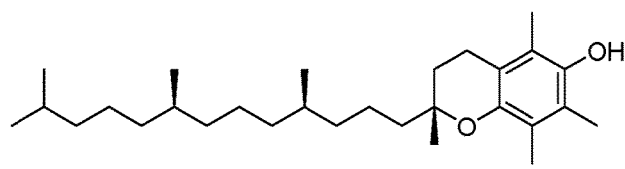
Alpha-tocopherol (Vitamin E)
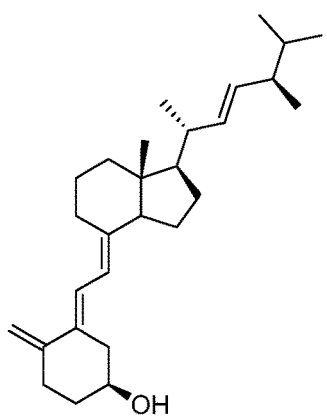
Calciferol (Vitamin D$_2$)
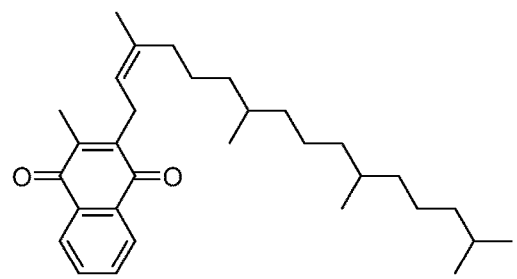
Phylloquinone (Vitamin K$_1$)
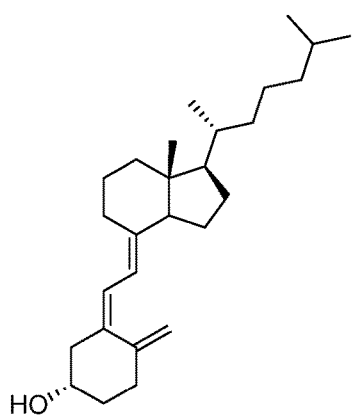
Cholecalciferol (Vitamin D$_3$)

LEVORPHANOL PRODRUGS AND PROCESSES FOR MAKING AND USING THEM

CROSS REFERENCE TO RELATED APPLICATIONS

This application is a continuation of U.S. patent application Ser. No. 16/604,710, filed on Oct. 11, 2019 which is a National Stage Entry of International Patent Application No. PCT/US2018/027263 which was filed Apr. 12, 2018 which claims priority to U.S. provisional application No. 62/485,890, filed on Apr. 14, 2017 and U.S. provisional application No. 62/485,891, filed on Apr. 14, 2017, which are herein incorporated by reference in their entirety. This application is also related to U.S. provisional application No. 62/485,888, filed on Apr. 14, 2017, which is herein incorporated by reference; and related to U.S. provisional application No. 62/485,894, filed on Apr. 14, 2017.

BACKGROUND OF THE INVENTION

Opioids are highly effective as analgesics and are commonly prescribed for the treatment of acute and chronic pain. They are also commonly used as antitussives. The opioids, however, also produce euphoria and are highly addictive. As a result, they are often abused with far reaching social and health related consequences.

Because of the inherent potential for abuse, it is desirable that any pharmaceutical composition containing an opioid agonist be made as abuse-resistant or abuse-deterrent as practical. Illicit users often will attempt to circumvent the extended release properties of these dosage forms by injecting or otherwise misusing the product in order to achieve an immediate release of the opioid agonist.

Levorphanol ((−)-17-methylmorphinan-3-ol) is the (−)-isomer and one of two enantiomers of 17-methylmorphinan-3-ol. The other enantiomer is dextrorphan ((+)-17-methylmorphinan-3-ol). A 1:1 mixture of both enantiomers (levorphanol and dextrorphan) is referred to as racemorphan.

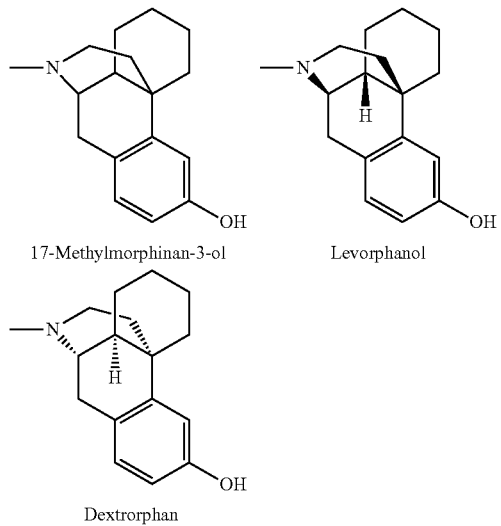

17-Methylmorphinan-3-ol    Levorphanol

Dextrorphan

It should be appreciated by those skilled in the art that different stereochemistry may impact the pharmacodynamics, pharmacological and/or pharmacokinetic properties, among other properties, of each isomer or racemic mixture utilized. Further, it should also be appreciated that various conjugations of the isomers to various ligands may also impact the pharmacodynamics, pharmacological and/or pharmacokinetic properties, among other properties, of each resultant conjugate, formulation, and/or end product. For example, those skilled in the art can appreciate the pharmacodynamics, pharmacological and/or pharmacokinetic property differences exhibited and/or observed by different enantiomers (levorphanol and dextrorphan) as well as a mixture such as racemorphan. Moreover, those skilled in the art also appreciate that the conjugation of those various different enantiomers may impact the various properties observed for the resultant levorphanol or dextrorphan conjugate, formulation and/or end product. Furthermore, those skilled in the art can recognize that conjugation to levorphanol, dextrorphan, or a mixture thereof, may create new enantiomers or diastereomers that may affect their resulting pharmacodynamic, pharmacological and/or pharmacokinetic properties.

Levorphanol is a narcotic analgesic, which interacts predominantly with receptors in the central nervous system (CNS). It has a wide range of pharmacological activities including μ-opioid agonism, (μ-opioid receptor (MOR)), δ-opioid receptor agonism (DOR), $κ_1$ and $κ_2$-opioid receptor agonism (KOR), and the nociceptin receptor (NOP), as well as an NMDA (N-methyl-D-aspartate) receptor antagonist and a reuptake inhibitor of both serotonin-norepinephrine (SNRI) and norepinephrine. This multimodal pharmacological profile may be effective for the treatment of CNS conditions including, but not limited to, pain, neuropathic pain, cancer pain, opioid-induced hyperalgesia, pain syndromes that are refractory to other analgesic medications, post-therapeutic neuralgia, depression, narcolepsy and hyperalgesia.

The present technology utilizes covalent conjugation of the opioid levorphanol with certain oxoacids, polyethylene glycols (PEG or PEO), and/or vitamin compounds to decrease its potential for causing overdose or abuse by requiring the active levorphanol to be released through enzymatic or metabolic breakdown of the conjugate in vivo. The present technology also provides methods of delivering levorphanol as conjugates that release the levorphanol following oral administration while being resistant to abuse by circuitous routes such as intravenous ("shooting") injection and intranasal administration ("snorting"). The compounds and conjugates of this disclosure (aka prodrugs) may be administered alone, or combined with other CNS agents, for the treatment of CNS conditions, including, but not limited to, pain, neuropathic pain, cancer pain, opioid-induced hyperalgesia, pain syndromes that are refractory to other analgesic medications, post-therapeutic neuralgia, depression, narcolepsy and hyperalgesia.

BRIEF SUMMARY OF THE INVENTION

The present technology utilizes conjugation of the opioid levorphanol with certain oxoacids, polyethylene glycols (PEG or PEO), and/or vitamin compounds to decrease its potential for causing overdose or abuse by requiring the active levorphanol to be released through enzymatic or metabolic breakdown of the conjugate in vivo. The present technology also provides methods of delivering levorphanol as conjugates that release the levorphanol following oral administration while being resistant to abuse by circuitous routes such as intravenous ("shooting") injection and intranasal administration ("snorting").

Advantages of certain embodiments of the levorphanol prodrugs of the present technology include, but are not limited to, reduced drug abuse potential, reduced or eliminated opioid induced constipation (OIC), reduced risk of chemical or physical manipulation resulting in full dosage of levorphanol release, reduced patient to patient variability in plasma concentrations compared to free levorphanol, improved dosage forms through modifications of the physical and chemical properties of the prodrugs.

In some aspects, the present technology provides an immediate release composition of conjugated levorphanol that allows delivery of the levorphanol into the blood system of a human or animal in a therapeutically bioequivalent manner upon oral administration. In at least one aspect, the compositions/formulations of the current technology can lessen common side effects associated with unconjugated levorphanol and similar compounds. The presently described technology, in at least one aspect, provides a slow/sustained/controlled release composition of conjugated levorphanol that allows slow/sustained/controlled delivery of the levorphanol into the blood system of a human or animal within a therapeutic window upon, for example, oral administration.

In one aspect, the present technology provides a composition comprising at least one conjugate of levorphanol, and at least one oxoacid, polyethylene glycol, vitamin compound, derivatives thereof, or combinations thereof. In some aspects, the conjugate further comprises a linker, wherein the linker chemically bonds the at least one levorphanol with the at least one oxoacid, polyethylene glycol, vitamin compound, or derivatives thereof.

In another aspect, the present technology provides at least one conjugate of levorphanol, and at least one oxoacid, polyethylene glycol, vitamin compound, derivatives thereof, or combinations thereof. In some aspects, the conjugate further comprises a linker, wherein the linker chemically bonds the at least one levorphanol with the at least one oxoacid, polyethylene glycol, vitamin compound, or derivatives thereof.

In one embodiment, the present technology provides a composition comprising at least one conjugate of levorphanol, wherein the conjugate has the following general Formula IA:

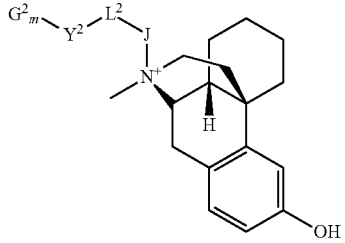

Formula IA where $L^2$ is absent, or is

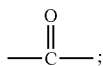

$Y^2$ is absent, or $[A-X—Z]n$ where A, X, Z are independently absent or selected from —O—, —S— or —$(CR^1R^2)_k$—

J is $[M-W]_p$ where M is absent or —$(CR^3R^4)_q$—; and W is absent, or —O— or —S—

$R^1$ and $R^2$ are each independently selected from H, alkyl, aryl, alkylaryl, alkoxy, haloalkyl, or haloaryl $R^3$ and $R^4$ are each independently selected from H, alkyl, aryl, alkylaryl, alkoxy, haloalkyl, or haloaryl n and k are independently 1-4 p and q are independently 1-4

$G^2_m$ is absent or selected independently for each repeating subunit from H, oxoacid, polyethylene glycol having from 2 to 5 ethylene oxide units, or a vitamin compound, and m is 1-4, except that m is 1 when $G^2$ is a hydrogen atom;

or a pharmaceutically acceptable salt thereof.

In another embodiment, the present technology provides a composition comprising at least one conjugate of levorphanol, wherein the conjugate has the following general Formula IB:

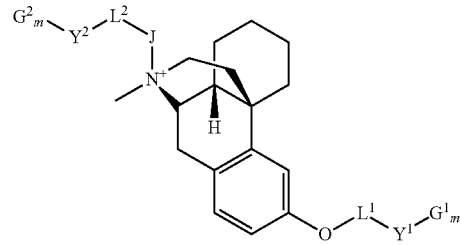

Formula IB where $L^1$ and $L^2$ are independently absent, or

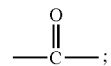

$Y^1$ and $Y^2$ are independently either absent, or $[A-X—Z]_n$ where A, X, Z are independently selected for $Y^1$ and $Y^2$, and are, independent of each other, either absent or selected from —O—, —S—, or —$(CR^1R^2)_k$—

J is $[M-W]_p$ where M is absent or —$(CR^3R^4)_q$—; and W is absent, or —O— or —S—

$R^1$ and $R^2$ are each independently selected for $Y^1$ and $Y^2$, and are, independent of each other, selected from H, alkyl, aryl, alkylaryl, alkoxy, haloalkyl, or haloaryl $R^3$ and $R^4$ are each independently selected from H, alkyl, aryl, alkylaryl, alkoxy, haloalkyl, or haloaryl for each $Y^1$ and $Y^2$, n is independently an integer of 1-4.

for each repeating unit of $[A-X—Z]_n$, when —$(CR^1R^2)_k$— is present, k is independently an integer of 1-4 p and q are independently 1-4

$G^1_m$ and $G^2_m$ are independently absent, or selected independently of each other and, when present, each repeating subunit is independently selected from H, oxoacid, polyethylene glycol having from 2 to 5 ethylene oxide units, or a vitamin compound;

where m is selected independently for $G^1$ and $G^2$, and is an integer of 1-4, except that m is 1 when $G^1$ or $G^2$ is a hydrogen atom;

or a pharmaceutically acceptable salt thereof.

In another aspect, the present technology provides at least one prodrug or conjugate having the structure of general Formula 1A or 1B.

In another aspect, the present technology provides at least one prodrug composition comprising at least one conjugate of levorphanol, derivatives thereof or combinations thereof, and at least one oxoacid, polyethylene glycol, vitamin compound, or derivatives thereof chemically bonded to levorphanol at either the N-17 tertiary amine position, or both the C-3 hydroxyl and the N-17 tertiary amine positions. In some embodiments, the prodrug composition may also comprise conjugate combinations and/or one or more active ingredients, additives, adjuvants, or combinations thereof.

In another aspect, the present technology provides at least one prodrug composition comprising at least one conjugate, wherein levorphanol is conjugated at the N-17 position, and wherein the at least one conjugate can be, for example, N-(acetyl-$OCH_2$)-levorphanolium; N-(pivaloyl-$OCH_2$)-levorphanolium; N-(Ser-Ile-$CH_2$)-levorphanolium; N-(Val-$CH_2$)-levorphanolium; N-(Phe-Val-$CH_2$)-levorphanolium; N-(MeO-$PEG_3$-$CH_2$C(O)$OCH_2$)-levorphanolium; N-(HO-$PEG_4$-$CH_2CH_2$C(O)$CH_2$)-levorphanolium; N-(BzO-$CH_2$OC(O)$OCH_2$)-levorphanolium; N-(Ala-$CH_2$OC(O)$OCH_2$)-levorphanolium; N-(Pro-Val-$CH_2$OC(O)$OCH_2$)-levorphanolium; N-(thiaminyl-C(O)$OCH_2$)-levorphanolium; N-(cinnamoyl-$OCH_2$SC(O)$SCH_2$)-levorphanolium; and anionic salts thereof, including hydrochloride/chloride salts.

In another aspect, the present technology provides at least one prodrug composition comprising at least one conjugate, wherein levorphanol is conjugated at both the C-3 hydroxyl and the N-17 position. The at least one conjugate can be, for example, 3-acetyl-N-(acetyl-$OCH_2$)-levorphanolium; 3-(pivaloyl)-N-(pivaloyl-$OCH_2$)-levorphanolium; 3-(ethoxy-C(O))—N-(ethoxy-C(O)CH($CH_3$))-levorphanolium; 3-(EtO—C(O))—N—($H_2$N-$PEG_2$-$CH_2CH_2$C(O)$OCH_2$)-levorphanolium; 3-(Ac-Val)-N-(PhePhe-$CH_2$)-levorphanolium; 3-(acetylsalicyloyl-$OCH_2$OC(O))—N-(Ac-Val-$CH_2$)-levorphanolium; 3-(Phe-CH(Me)C(O))—N-(nicotinoyl-$OCH_2$)-levorphanolium, and anionic salts thereof, including hydrochloride/chloride salts.

In yet another aspect, the present technology provides a method for chemically synthesizing any of the levorphanol conjugates of the present technology by performing the appropriate steps to conjugate levorphanol to at least one ligand.

In a further aspect, the present technology provides a method for treating a human or animal patient having a disease, disorder or condition requiring or mediated by binding of an opioid to the opioid receptors, or by binding of an NMDA receptor antagonist to the NMDA receptors of the patient, comprising orally administering to the patient a pharmaceutically effective amount of at least one levorphanol conjugate of the present technology.

In another aspect, the present technology provides a pharmaceutical kit comprising a specified amount of individual doses in a package, each dose comprising a pharmaceutically effective amount of at least one conjugate of levorphanol.

BRIEF DESCRIPTION OF THE DRAWINGS

FIG. 5. Chemical structures of some benzylacetates for use in the making of the conjugates of the present technology.

FIG. 7. Chemical structures of some dicarboxylic acids for use in the making of the conjugates of the present technology.

FIG. 8. Chemical structures of some tricarboxylic acids for use in the making of the conjugates of the present technology.

FIG. 9. Chemical structures of some standard amino acids for use in the making of the conjugates of the present technology.

FIG. 11. Chemical structures of some synthetic amino acids for use in the making of the conjugates of the present technology.

FIG. 12A. Chemical structures of some water soluble vitamins for use in the making of the conjugates of the present technology.

FIG. 12B. Chemical structures of some fat soluble vitamins for use in the making of the conjugates of the present technology.

DETAILED DESCRIPTION

Figure 1:
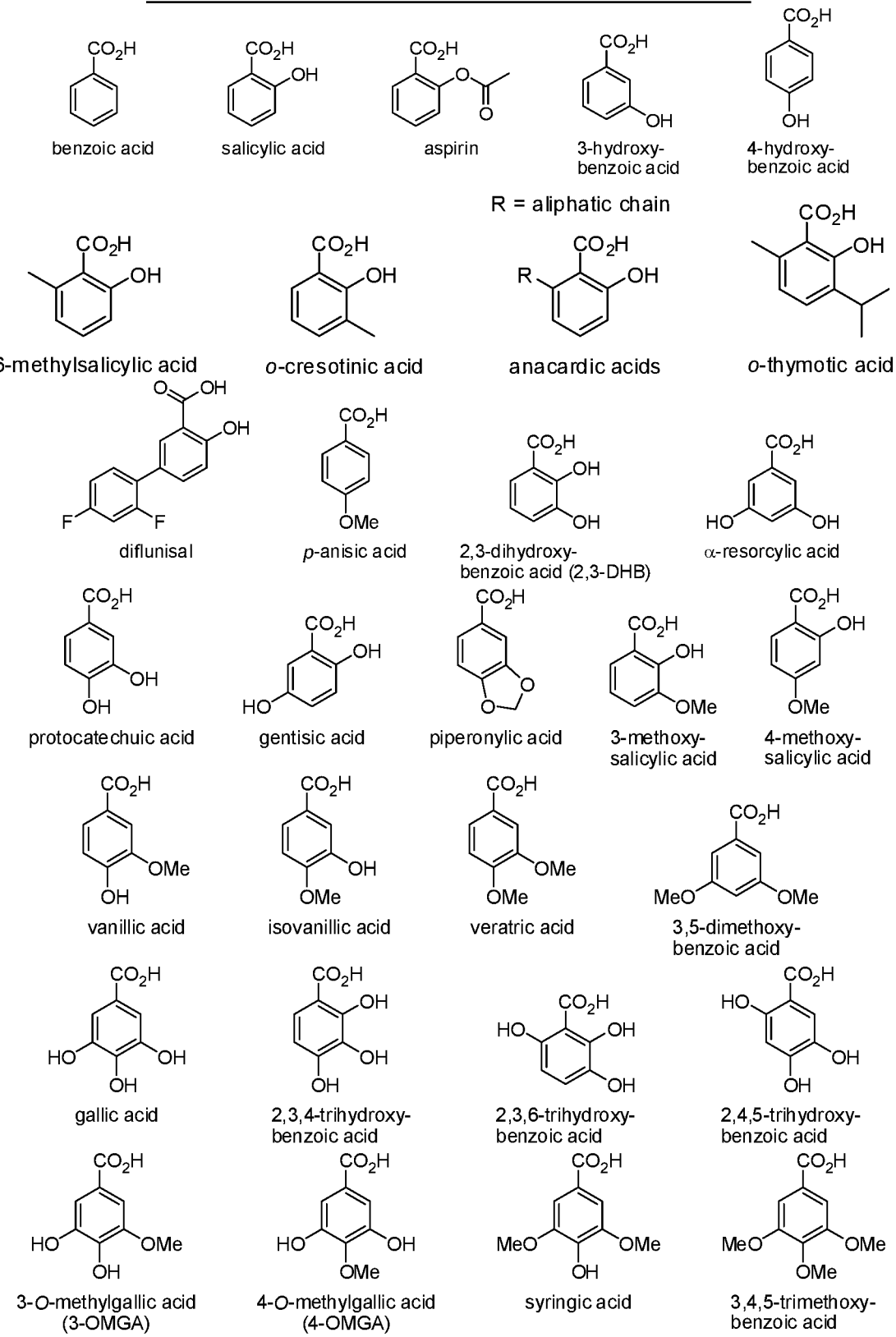
FIG. 1. Chemical structures of some hydroxybenzoates for use in the making of the conjugates of the present technology.

The present technology provides compounds of, or compositions comprising oxoacids, polyethylene glycols (PEG or PEO), and/or vitamin compounds ("ligands") chemically conjugated to levorphanol to form novel prodrugs and conjugates of levorphanol. The ligands are covalently bonded to either the N-17 tertiary amine of levorphanol, or both the C-3 hydroxyl and the N-17 tertiary amine of levorphanol, either directly or through one or more linkers, to form the levorphanol conjugates.

In some embodiments, the chemical connection between the ligands and levorphanol can be established at the N-17 tertiary amine of levorphanol through an N-alkyl linker by an alkylation reaction at the N-17 tertiary amine to form a quaternary ammonium salt or levorphanolium salt. In some embodiments, the oxoacids, polyethylene glycols, and/or vitamin compounds are directly connected to this N-alkyl linker. In other embodiments, a second linker is attached to the first N-alkyl linker and the oxoacids, polyethylene glycols, and/or vitamin compounds are directly connected to the second linker. In further embodiments, the second linker may comprise an alcohol, hydroxyacid, or hydroxyamino acid.

In some other embodiments, the ligands are covalently bonded or connected to both the C-3 hydroxyl and the N-17 tertiary amine of levorphanol. In such embodiments, the chemical connection between the ligands and levorphanol can be established at the N-17 tertiary amine by any of the reactions described above. The chemical bond between the ligands and the C-3 hydroxyl in some embodiments can be established by reacting the C-3 hydroxyl of levorphanol with the activated carboxylic acid function of an oxoacid or some vitamin compounds. In other embodiments, the hydroxyl group of an alcohol, hydroxyacid, hydroxyamino acid, or some vitamin compounds is conjugated to C-3 of levorphanol. In further embodiments, a hydroxyacid is used as a linker that is connected to C-3 of levorphanol on one end (by reaction with its hydroxyl group) and to an alcohol, hydroxyacid, hydroxyamino acid, or vitamin compound on the other end (by reaction with its carboxyl group). In yet further embodiments, a dicarboxylic acid can be used as linker that is connected to the C-3 of levorphanol on one end and to an alcohol, hydroxyacid, hydroxyamino acid, or vitamin compound on the other end. It should be understood by one of skill in the art that the ligands can be attached at both the C-3 and N-17 positions in either order, i.e. attachment at the C-3 hydroxyl followed by attachment at the N-17 alkyl amine, or vice versa.

The use of "opioid" is meant to include any drug that activates the opioid receptors found in the brain, spinal cord and gut. There are four broad classes of opioids: naturally occurring opium alkaloids, such as morphine (the prototypical opioid) codeine, and thebaine; endogenous opioid peptides, such as endorphins; semi-synthetics such as heroine, oxycodone and hydrocodone that are produced by modifying natural opium alkaloids (opiates) and have similar chemical structures; and pure synthetics such as fentanyl and methadone that are not produced from opium and may have very different chemical structures than the opium alkaloids. Additional examples of opioids are hydromorphone, oxymorphone, methadone, levorphanol, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

The use of the term "levorphanol" herein means (−)-17-methylmorphinan-3-ol, including all salt forms thereof. In some embodiments, the conjugates contain levorphanol in a racemic mixture (racemorphan). In other embodiments, the levorphanol conjugates are not in a racemic mixture. Depending on the chemical structure of the linkers and oxoacids, polyethylene glycol (PEG or PEO), and/or vitamin compounds, as well as the chiral composition of the levorphanol to which they are attached, the resulting prodrug conjugates can be optically active mixtures of isomers, racemic mixtures, single isomers or combinations thereof.

As used herein, "normative patient" as used herein means a patient that, in general, meets or requires standard and/established treatment modalities, treatment guidelines, prescribing guidelines, among others to achieve a variety of pharmaceutical and/or therapeutic outcomes.

As used herein, the term "conjugate" means a compound or substance formed by bonding two or more chemical compounds or substances in such a way that the bonding is reversible in vivo. For example, a conjugate is the resultant compound formed by bonding at least one pharmaceutical or therapeutically active ingredient with at least one ligand, such as at least one oxoacid, or other substance or compound capable of being a ligand, which is then broken down in vivo into the pharmaceutical or therapeutically active ingredient and ligand. One skilled in the art will appreciate that the term "conjugate" is used in a non-limiting manner and includes various forms including salts, polymorphs, among others.

As used herein, the term "prodrug" refers to a substance converted from an inactive or less active form of a drug to an active drug in the body by a chemical or biological reaction. In the present technology, the prodrug is a conjugate of at least one drug, levorphanol, and at least one oxoacid, for example. Thus, the conjugates of the present technology are prodrugs and the prodrugs of the present technology are conjugates.

Prodrugs are often useful because, in some embodiments, they may be easier to administer or process than the parent drug. They may, for instance, be more bioavailable by oral administration whereas the parent drug is not. The prodrug may also have improved solubility in pharmaceutical compositions over the parent drug. An embodiment of a prodrug would be a levorphanol conjugate that is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug is designed to alter the metabolism, pharmacokinetics, or the transport characteristics of a drug in certain embodiments, to reduce or lessen side-effects or toxicity, to improve bioavailability and/or water solubility, to improve the flavor of a drug or to alter other characteristics or properties of a drug in other discrete embodiments.

In some embodiments, the present technology provides at least one prodrug composition comprising at least one conjugate. The at least one conjugate may comprise at least one levorphanol and at least one oxoacid, polyethylene glycol, vitamin compound, derivatives thereof, or combinations thereof. In some embodiments, the conjugate further comprises at least one linker. The linker chemically bonds the levorphanol to the oxoacid, polyethylene glycol, or vitamin compound via one or more covalent bonds.

Depending on the linker and the oxoacid, polyethylene glycol, and/or vitamin compound conjugated to levorphanol or derivative thereof, the at least one prodrug formed can be either a neutral (uncharged), a free acid, a free base or a pharmaceutically acceptable anionic salt form or salt mixtures with any ratio between positive and negative components. These anionic salt forms can include, but are not limited to, for example, acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, i-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, or undecylenate.

Without wishing to be limited to the following theory, it is believed that the prodrugs/conjugates of the present technology undergo enzyme hydrolysis of the ligand/linker-levorphanol bond(s) in vivo, which subsequently leads to a cascade reaction resulting in rapid regeneration of levorphanol and the respective oxoacid, polyethylene glycol, vitamin compound, or metabolites thereof and/or derivatives thereof. The oxoacids, polyethylene glycols, vitamin compounds, or derivatives thereof, of the present technology are non-toxic or have very low toxicity at the given dose levels and are preferably known drugs, natural products, metabolites, or GRAS (Generally Recognized As Safe) compounds (e.g., preservatives, dyes, flavors, etc.) or non-toxic mimetics or derivatives thereof.

General Structures

In some embodiments, the general structure of the prodrugs of levorphanol of the present technology can be represented by the following general Formula IA:

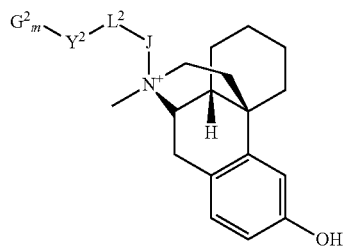

Formula 1A where $L^2$ is absent, or is

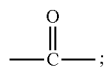

$Y^2$ is absent, or $[A\text{-}X\text{—}Z]_n$ where A, X, Z are independently absent or selected from —O—, —S— or —$(CR^1R^2)_k$—

J is $[M\text{-}W]_p$ where M is absent or —$(CR^3R^4)_q$—; and W is absent, or —O— or —S—

$R^1$, $R^2$, $R^3$, $R^4$ are each independently selected from H, alkyl, aryl, alkylaryl, alkoxy, haloalkyl, or haloaryl n and k are independently 1-4 p and q are independently 1-4

$G_m^2$ is absent or selected independently for each repeating subunit from H, oxoacid, polyethylene glycol having from 2 to 5 ethylene oxide units, or a vitamin compound, and m is 1-4, except that m is 1 when $G^2$ is a hydrogen atom;

or a pharmaceutically acceptable salt thereof.

In some embodiments, M is —$(CR^3R^4)_q$—, W, $L^2$ and $Y^2$ are absent, $G^2$ is an oxoacid, and m is 1-3. Representative examples include, but are not limited to N-(acetyl-OCH$_2$)-levorphanolium; N-(pivaloyl-OCH$_2$)-levorphanolium; N-(Ser-Ile-CH$_2$)-levorphanolium; N-(Val-CH$_2$)-levorphanolium; and N-(Phe-Val-CH$_2$)-levorphanolium.

In some embodiments, M is —$(CR^3R^4)_q$—, W is —O—, L is present, A is —$CR^1R^2$—, X is absent, Z is absent or —$CR^1R^2$—, G is polyethylene glycol. Representative examples include, but are not limited to N-(MeO-PEG$_3$-CH$_2$C(O)OCH$_2$)-levorphanolium and N-(HO-PEG$_4$-CH$_2$CH$_2$C(O)CH$_2$)-levorphanolium.

In some embodiments, M is —$(CR^3R^4)_q$—, W is —O—, $L^2$ is present, A is —O—, X is —$(CR^1R^2)_k$—, $G^2$ is an oxoacid, and m is 1-3. Representative examples include, but are not limited to N-(BzO-CH$_2$OC(O)OCH$_2$)-levorphanolium; N-(Ala-CH$_2$OC(O)OCH$_2$)-levorphanolium; and N-(Pro-Val-CH$_2$OC(O)OCH$_2$)-levorphanolium.

In some embodiments, M is —$(CR^3R^4)_q$—, W is —O—, $L^2$ is present, A is —O—, X and Z are absent, $G^2$ is a vitamin compound, and m is 1-3.

In some other embodiments, the general structure of the conjugates of levorphanol of the present technology can be represented by the following general Formula IB:

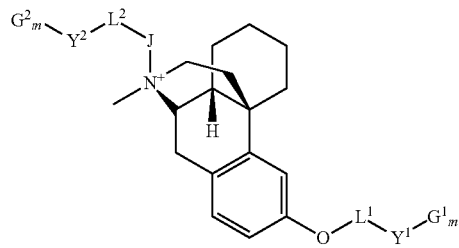

Formula IB where $L^1$ and $L^2$ are independently absent, or

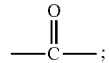

$Y^1$ and $Y^2$ are independently either absent, or $[A\text{-}X\text{—}Z]_n$ where A, X, Z are independently selected for $Y^1$ and $Y^2$, and are, independent of each other, either absent or selected from the group of —O—, —S—, or —$(CR^1R^2)_k$—

J is $[M\text{-}W]_p$ where M is absent or —$(CR^3R^4)_q$—; and W is absent, or —O— or —S—

$R^1$ and $R^2$ are each independently selected for $Y^1$ and $Y^2$, and are, independent of each other, selected from H, alkyl, aryl, alkylaryl, alkoxy, haloalkyl, or haloaryl $R^3$ and $R^4$ are each independently selected from H, alkyl, aryl, alkylaryl, alkoxy, haloalkyl, or haloaryl for each $Y^1$ and $Y^2$, n is independently an integer of 1-4.

for each repeating unit of $[A\text{-}X\text{—}Z]_n$, k is independently an integer of 1-4.

p and q are independently 1-4

$G_m^1$ and $G_m^2$ are independently absent, or selected independently of each other and when present, each repeating subunit is independently selected from H, oxoacid, polyethylene glycol having from 2 to 5 ethylene oxide units, or a vitamin compound;

where m is selected independently for $G^1$ and $G^2$, and is an integer of 1-4, except that m is 1 when $G^1$ or $G^2$ is a hydrogen atom;

or a pharmaceutically acceptable salt thereof.

In some embodiments, $L^1$ and $Y^1$ are absent, $G^1$ is an oxoacid and m is 1-3, and M is —$(CR^3R^4)_q$—; W, $L^2$ and $Y^2$ are absent, $G^2$ is an oxoacid, and m is 1-3. Representative examples include 3-(pivaloyl)-N-(pivaloyl-$OCH_2$)-levorphanolium; 3-(Ac-Val)-N-(PhePhe-$CH_2$)-levorphanolium; 3-(Ser-Ile)-N-(Val-$CH_2$)-levorphanolium; 3-Val-N-(Val-$CH_2$)-levorphanolium;

In some embodiments, $L^1$ and $Y^1$ are present, A is O, X is —$(CR^1R^2)_k$—, Z is O, $G_m^1$ is an oxoacid, and m is 1-3, and M is —$(CR^3R^4)_q$—; W, $L^2$ and $Y^2$ are absent, $G^2$ is an oxoacid, and m is 1-3. Representative examples include 3-(acetylsalicyloyl-$OCH_2OC(O)$)—N-(Ac-Val-$CH_2$)-levorphanolium.

In some embodiments, $L^1$ is present, $Y^1$ is present, where A is —$(CR^1R^2)_k$—, X and Z are absent, and $G^1$ is H, and M is —$(CR^3R^4)_q$—, W, $L^2$ and $Y^2$ are absent, $G^2$ is an oxoacid, and m is 1-3. Representative examples include 3-acetyl-N-(acetyl-$OCH_2$)-levorphanolium.

In some embodiments, $L^1$ is present, $Y^1$ is present, where A is O, X and Z are —$(CR^1R^2)_k$—, and $G^1$ is H, and M is —$(CR^3R^4)_q$—, W is absent, $L^2$ and $Y^2$ are present, where A is O, X and Z are —$(CR^1R^2)_k$—, and $G^2$ is H. Representative examples include 3-(ethoxy-C(O))—N-(ethoxy-C(O)CH($CH_3$))-levorphanolium.

Oxoacids

Organic oxoacids (i.e., oxyacids, oxo acids, oxy-acids, oxiacids, oxacids) of the present technology are a class of compounds which contain oxygen, at least one other element, and at least one hydrogen bound to oxygen, and which produce a conjugate base by loss of positive hydrogen ion(s) (protons). Organic acids include carboxylic acids. Carboxylic acids are widespread in nature (naturally occurring), but carboxylic acids can also be non-natural (synthetic). Carboxylic acids can be categorized into numerous classes based on their molecular structure or formula, and many of the different classes may overlap.

Without wishing to limit the scope to one classification, the carboxylic acids of the present technology can be grouped into the following categories: aryl carboxylic acids, aliphatic carboxylic acids, dicarboxylic, polycarboxylic acids, and amino acids.

Some embodiments of the present technology provide oxoacids conjugated to levorphanol, where the carboxylic acid group is directly attached to an aryl moiety. Carboxylic acids directly attached to the aryl moiety include benzoates and heteroaryl carboxylic acids. Benzoates are common in nature and include, for example but are not limited to, aminobenzoates (e.g., anthranilic acid analogs such as fenamates), aminohydroxybenzoates and hydroxybenzoates (e.g., salicylic acid analogs).

The general structure of benzoic acid and benzoic acid derivatives of the present technology can be represented by the following Formula II:

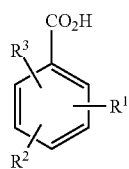

Formula II

In this Formula II, $R^1$, $R^2$, $R^3$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, and phosphonate.

Suitable hydroxybenzoic acids can be found in FIG. 1 and include, but are not limited to, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflunisal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, 3,4,5-trimethoxybenzoic acid.

Figure 2:
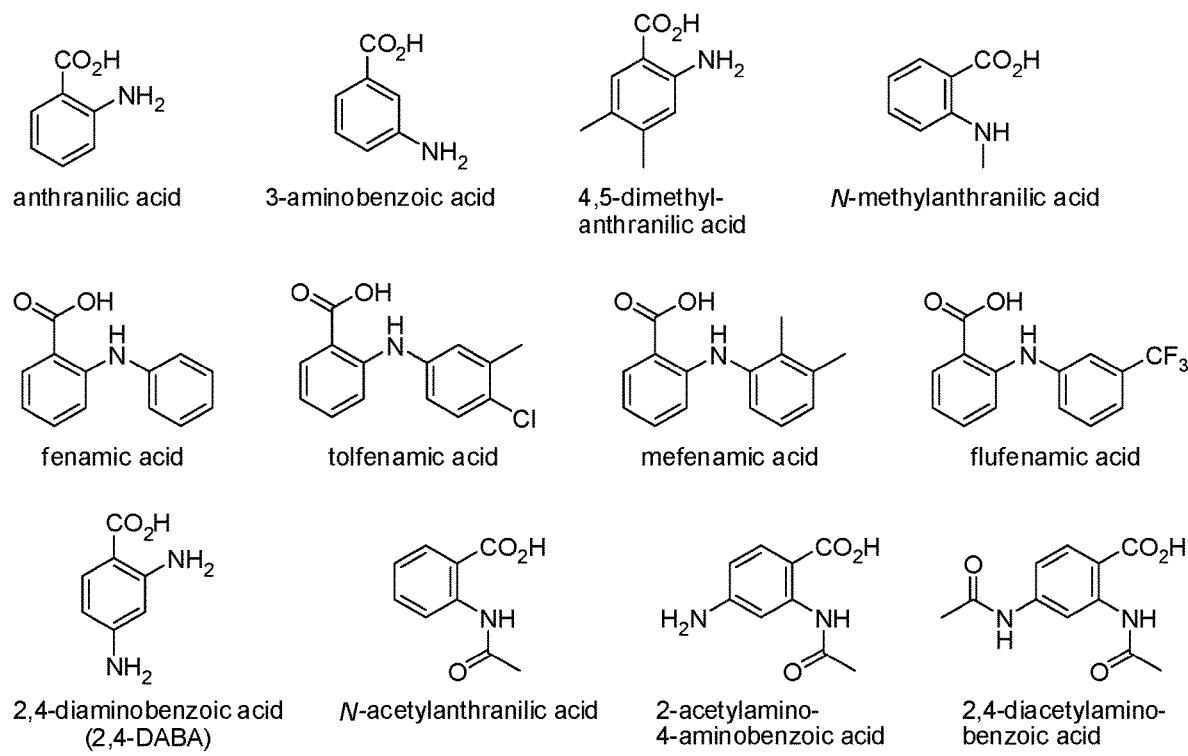
FIG. 2. Chemical structures of some aminobenzoic acids for use in the making of the conjugates of the present technology.

Suitable aminobenzoic acids are shown in FIG. 2 and include, but are not limited to, anthranilic acid, 3-aminobenzoic acid, 4,5-dimethylanthranilic acid, N-methylanthranilic acid, N-acetylanthranilic acid, fenamic acids (e.g., tolfenamic acid, mefenamic acid, flufenamic acid), 2,4-diaminobenzoic acid (2,4-DABA), 2-acetylamino-4-aminobenzoic acid, 4-acetylamino-2-aminobenzoic acid, 2,4-diacetylaminobenzoic acid.

Suitable aminohydroxybenzoic acids include, but are not limited to, 4-aminosalicylic acid, 3-hydroxyanthranilic acid, 3-methoxyanthranilic acid.

In some embodiments, the composition includes a benzoate conjugate comprising at least one levorphanol conjugated to at least one benzoic acid or benzoic acid derivative, salt thereof or combination thereof.

In some embodiments, the benzoates include numerous benzoic acid analogs, benzoate derivatives with hydroxyl or amino groups or a combination of both. The hydroxyl and amino functions may be present in their free form or capped with another chemical moiety, preferably but not limited to methyl or acetyl groups. The phenyl ring may have additional substituents, but the total number of substituents can be four or less, three or less, or two or less.

In yet another embodiment, the present technology provides a prodrug or composition comprising at least one conjugate of levorphanol and at least one heteroaryl carboxylic acid, a derivative thereof, or a combination thereof. The heteroaryl carboxylic acid can be selected from Formula III, Formula IV, Formula V, Formula VI, Formula VII, Formula VIII, Formula IX, Formula X, or Formula XI, where Formula III, Formula IV, Formula V, Formula VI, Formula VII, Formula VIII, Formula IX, Formula X, or Formula XI are:

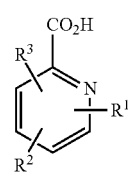

Formula III

-continued

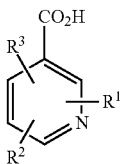

Formula IV

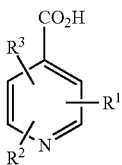

Formula V

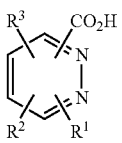

Formula VI

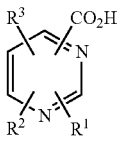

Formula VII

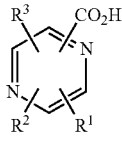

Formula VIII

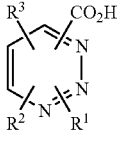

Formula IX

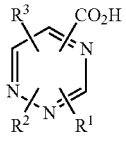

Formula X

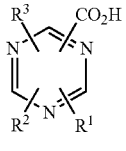

Formula XI

Figure 3:
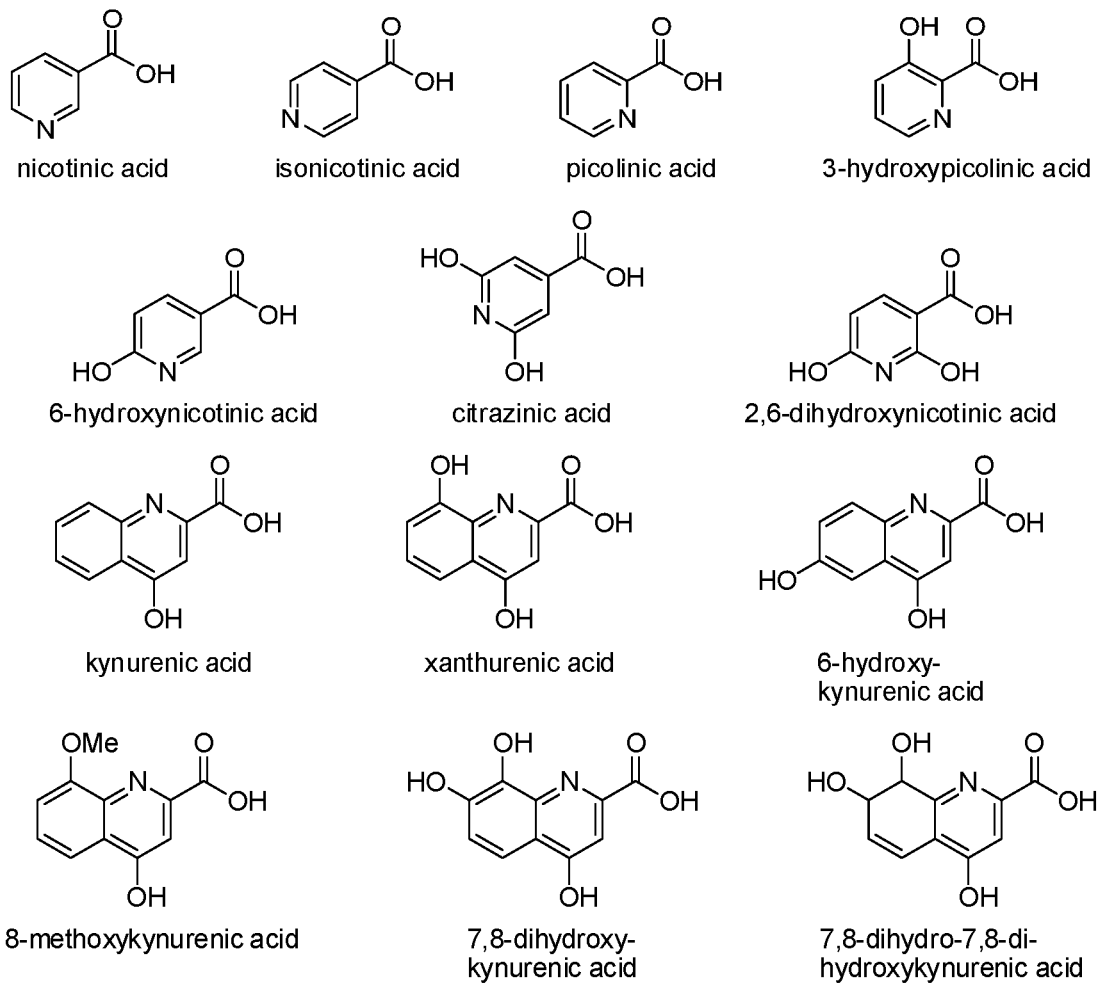
FIG. 3. Chemical structures of some heteroaryl carboxylic acids for use in the making of the conjugates of the present technology.

For these Formulas III, IV, V, VI, VII, VIII, IX, X, and XI, $R^1$, $R^2$, $R^3$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, and phosphonate. Some structures of suitable heteroaryl carboxylic acids for use in the present technology are found in FIG. 3.

In some embodiments, the carboxy group of the aryl carboxylic acids can be attached directly to the aromatic ring. The present technology includes both carbon-only aryl groups and aryl groups with heteroatoms (heteroaryl). The aryl or heteroaryl group which is connected directly to the carboxyl function can be a 6-membered ring and contains no or one heteroatom. In some embodiments, the additional substituted or unsubstituted aromatic or aliphatic rings can be fused to this 6-membered aryl or heteroaryl moiety. In some embodiments, the aryl carboxylic acids may have only one free carboxylic acid group and the total number of phenyl substituents on the 6-membered ring should be four or less, for example, 4, 3, 2 or 1.

Phenylacetates

Figure 4:
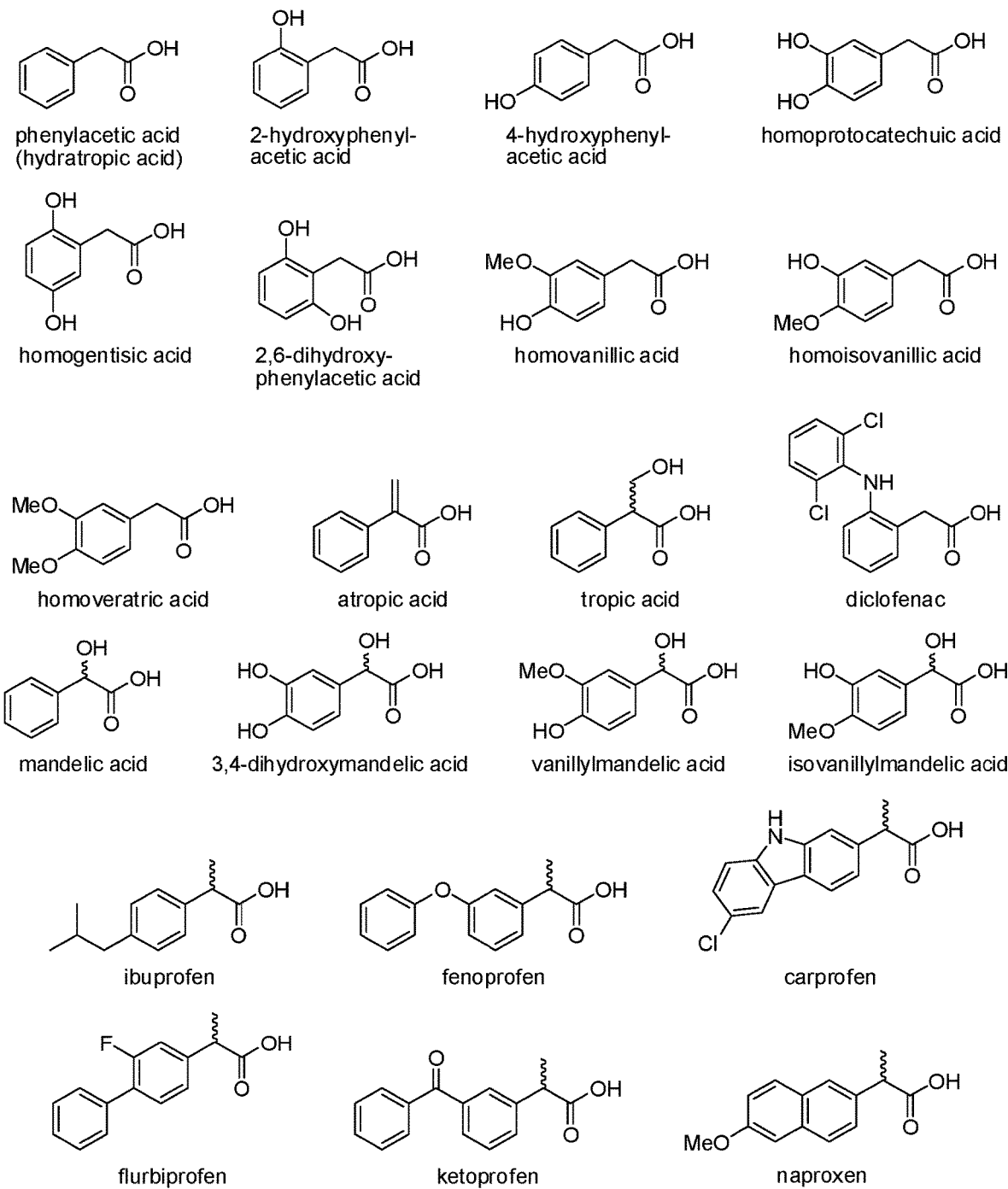
FIG. 4. Chemical structures of some phenylacetates for use in the making of the conjugates of the present technology.

In some embodiments of the present technology, the aryl carboxylic acids of the present technology comprise a carboxylic group that is separated by one carbon from the aryl moiety. These aryl carboxylic acids include branched phenylpropionic acids (i.e., 2-methyl-2-phenylacetates) or other derivatives of phenylacetate (FIG. 4). The general structure of at least one phenylacetate of the present technology is represented by the following general Formula XII:

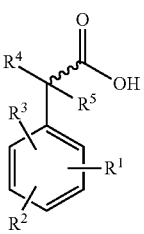

Formula XII

For this Formula XII, $R^1$, $R^2$, $R^3$, $R^4$, $R^5$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, and phosphonate.

Phenylacetic acids encompass various subsets of natural products, metabolites and pharmaceuticals. One such pharmaceutically important subset is "profens", a type of NSAIDs and derivatives of certain phenylpropionic acids (e.g., 2-methyl-2-phenylacetic acid analogs). Some other phenylacetates have central functions in the phenylalanine and tyrosine metabolism.

Some examples of phenylacetates of the present technology include, but are not limited to, phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, and naproxen. Some structures of suitable phenylacetates for use in the present technology are found in FIG. 4.

Benzylacetates

Figure 6:
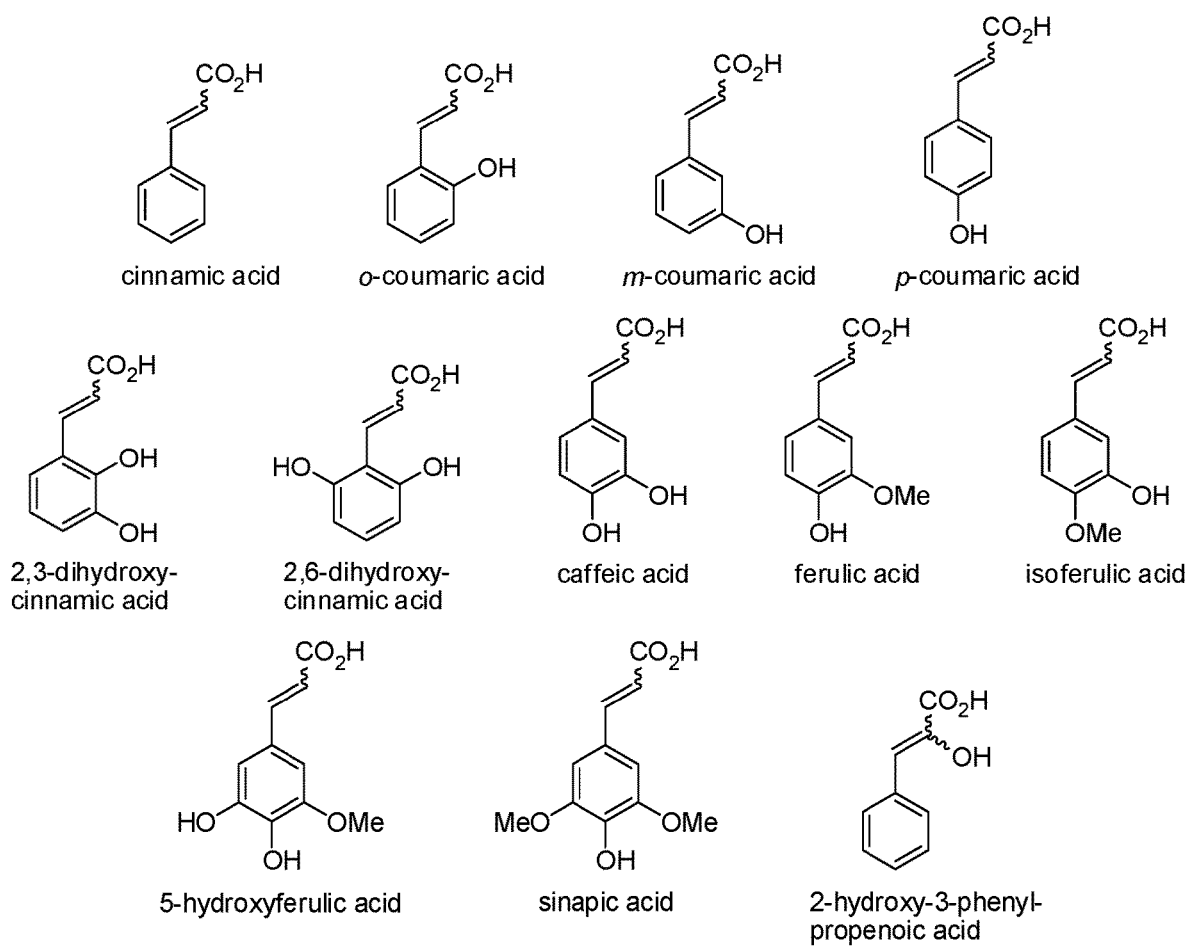
FIG. 6. Chemical structures of some cinnamates for use in the making of the conjugates of the present technology.

In additional embodiments, the aryl carboxylic acids of the present technology comprise a carboxylic group that is separated by two carbons from the aryl moiety. These aryl carboxylic acids include benzylacetates (FIG. 5) and substituted derivatives thereof and analogs of cinnamic acid (FIG. 6). Both classes of compounds are abundant in nature in the form of natural products or metabolites (e.g., phenylalanine metabolism). The general structures of some benzylacetates and cinnamates of the present technology are represented by the following general Formulas XIII and XIV:

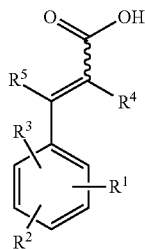

Formula XIII

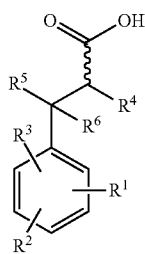

Formula XIV

For these Formulas XIII and XIV, $R^1$, $R^2$, $R^3$, $R^4$, $R^5$, $R^6$ are independently selected from the group consisting of H, hydroxyl, amino, amine, amide, thiol, cyano, nitro, halogen, imine, alkyl, alkoxy, aryl, alkenyl, alkynyl, haloalkyl, alkylaryl, arylalkyl, heterocycle, arylalkoxy, cycloalkyl, cycloalkenyl, cycloalkynyl, carbonyl, thioether, selenoether, silyl, silyloxy, sulfonyl, and phosphonate.

Benzylacetic acids are defined by an ethylene group between the carboxyl function and the phenyl ring. Both the alkyl chain and the aryl moiety can have substituents, preferably hydroxyl groups. Some compounds of this class can be found in the phenylalanine metabolism.

Some examples of benzylacetates of the present technology include, but are not limited to, benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, or phenylpyruvic acid.

Cinnamates

Cinnamic acids (3-phenylacrylic acids) (FIG. 6) are unsaturated analogs of benzylacetic acids. Cinnamates occur in two isomeric forms: cis (Z) and trans (E). The cinnamate isomers of certain embodiments of the present technology are preferably, but not limited to, the trans configuration. Similar to benzylacetates, derivatives of cinnamic acid can be substituted on the alkenyl or aryl moiety of the molecule. Preferred substituents of some embodiments of the present technology are hydroxyl and methoxy groups. Certain cinnamates are thought to play a key role in phenylalanine metabolism.

Some examples of cinnamates of the present technology include, but are not limited to, cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, or 2-hydroxy-3-phenylpropenoic acid.

Suitable aliphatic carboxylic acids for use in the present technology include, but are not limited to, for example, saturated, monounsaturated, polyunsaturated, acetylenic, substituted (e.g., alkyl, hydroxyl, methoxy, halogenated, etc.), heteroatom containing or ring containing carboxylic acids. Suitable examples of saturated carboxylic acids include, but are not limited to, for example, methanoic, ethanoic, propanoic, butanoic, pentanoic, hexanoic, heptanoic, octanoic, 2-propylpentanoic acid, nonanoic, decanoic, dodecanoic, tetradecanoic, hexadecanoic, heptadecanoic, octadecanoic, or eicosanoic acid. Suitable monounsaturated carboxylic acids for practice of the present technology include, but are not limited to, for example, 4-decenoic, 9-decenoic, 5-lauroleic, 4-dodecenoic, 9-tetradecenoic, 5-tetradecenoic, 4-tetradecenoic, 9-hexadecenoic, 6-hexadecenoic, 6-octadecenoic, or 9-octadecenoic acid.

Suitable polyunsaturated carboxylic acids for use in the present technology include, but are not limited to, for example, sorbic, octadecadienoic, octadecatrienoic, octadecatetraenoic, eicosatrienoic, eicosatetraenoic, eicosapentaenoic, docosapentaenoic, or docosahexaenoic acids. Suitable acetylenic carboxylic acids for use in the present technology include, but are not limited to octadecynoic, octadecenynoic, 6,9-octadecenynoic, heptadecenynoic, tridecatetraenediynoic, tridecadienetriynoic, octadecadienediynoic, heptadecadienediynoic, octadecadienediynoic, octadecenediynoic, or octadecenetriynoic acids.

Suitable substituted carboxylic acids for practice of the present technology include, but are not limited to, for example, methylpropanoic, isovaleric, methylhexadecanoic, 8-methyl-6-nonenoic, methyloctadecanoic, trimethyloctacosanoic, trimethyltetracosenoic, heptamethyltriacontanoic, tetramethylhexadecanoic, tetramethylpentadecanoic, lactic, glyceric, glycolic, threonic, 3-hydroxypropionic, hydroxyoctadecatrienoic, hydroxyoctadecenoic, hydroxytetracosanoic, 2-hydroxybutyric, 3-hydroxybutyric, 4-hydroxybutyric, 4-hydroxypentanoic, hydroxyoctadecadienediynoic, hydroxyoctadecadienoic, 10-hydroxydecanoic, hydroxydecenoic, hydroxyeicosenoic, hydroxyeicosadienoic, hydroxyhexadecanoic, dihydroxytetracosenoic, dihydroxydocosanoic, hydroxydocosanoic, trihydroxyoctadecanoic, trihydroxyhexadecanoic, trihydroxyicosahexaenoic, trihydroxyicosapentaenoic, 2-methoxy-5-hexadecenoic, 2-methoxy hexadecanoic, 7-methoxy-4-tetradecenoic, 9-methoxypentadecanoic, 11-methoxyheptadecanoic, 3-methoxydocosanoic, diacetoxydocosanoic, 2-acetoxydocosanoic, 2-acetoxytetracosanoic, 2-acetoxyhexacosanoic, 9-oxononanoic, oxodecanoic, oxododecenoic, hydroxyoxodecenoic, 10-oxo-8-decenoic, fluorooctadecenoic, fluorodecanoic, fluorotetradecanoic, fluorohexadecanoic, fluorooctadecadienoic, chlorohydroxyhexadecanoic, chlorohydroxyoctadecanoic, dichlorooctadecanoic, 3-bromo-2-nonaenoic, 9,10-dibromooctadecanoic, 9,10,12, 13-tetrabromooctadecanoic, 10-nitro-9,12-octadecadienoic, 12-nitro-9,12-octadecadienoic, 9-nitro-9-octadecenoic, 9-oxo-2-decenoic, 9-oxo-13-octadecenoic, oxooctadecatrienoic, 15-oxo-18-tetracosenoic, 17-oxo-20-hexacosenoic, or 19-oxo-22-octacosenoic acids.

Suitable examples of heteroatom containing carboxylic acids include, but are not limited to, for example, 9-(1,3-nonadienoxy)-8-nonenoic, 9-(1,3,6-nonatrienoxy)-8-nonenoic, 12-(1-hexenoxy)-9,11-dodecadienoic, 12-(1,3-hexadienoxy)-9,11-dodecadienoic, 2-dodecylsulfanylacetic, 2-tetradecylsulfanylacetic, 3-tetradecylsulfanylprop-2-enoic, or 3-tetradecylsulfanylpropanoic acid. Suitable examples of ring containing carboxylic acids include, but are not limited to, for example, 10-(2-Hexylcyclopropyl) decanoic, 3-(2-[6-bromo-3,5-nondienylcyclopropyl)propanoic, 9-(2-hexadecylcyclopropylidene)non-5-enoic, 8-(2-octyl-1-cyclopropenyl)octanoic, 7-(2-octyl-1-cyclopropenyl)heptanoic, 9,10-epoxyoctadecanoic, 9,10- epoxy12-octadecenoic, 12,13-epoxy-9-octadecenoic, 14,15-epoxy-11-eicosenoic, 11-(2-cyclopenten-1-yl)undecanoic, 13-(2-cyclopenten-1-yl)tridecanoic, 13-(2-cyclopentenyl)-6-tridecenoic, 11-cyclohexylundecanoic, 13-cyclohexyltridecanoic, 7-(3,4-dimethyl-5-pentylfuran-2-yl)heptanoic, 9-(4-methyl-5-pentylfuran-2-yl)nonanoic, 4-[5]-ladderane-butanoic, 6-[5]-ladderane-hexanoic, or 6-[3]-ladderane-hexanoic acid.

In some embodiments, the levorphanol, derivatives thereof or combinations thereof, can be conjugated to one or more dicarboxylic acids or tricarboxylic acids. Dicarboxylic acids are compounds with two carboxyl groups with a general formula of HOOC—R—COOH, where R can be an alkyl, alkenyl, alkynyl or aryl group, or derivatives thereof. Dicarboxylic acids can have straight carbon chains or branched carbon chains. The carbon chain length may be short or long. Polycarboxylic acids are carboxylic acids with three or more carboxyl groups. Suitable examples of dicarboxylic and tricarboxylic acids for the practice of the present technology include, but are not limited to, for example, oxalic, malonic, succinic, glutaric, adipic, pimelic, suberic, azelaic, sebacic, brassylic, thapsic, malic, tartaric, dihydroxymesoxalic, Q-hydroxyglutaric, methylmalonic, meglutol, diaminopimelic, carbamoyl aspartic, fumaric, maleic, mesaconic, 3-methylglutaconic, traumatic, phthalic acid, isophthalic, terephthalic, dipicolinic, citric acid, isocitric, carballylic, or trimesic acid. Some structures of suitable dicarboxylic acids for use in the practice of the present technology can be found in FIG. 7, and some structures of suitable tricarboxylic acids for use in the practice of the present technology can be found in FIG. 8.

Amino Acids

Amino acids are one of the most important building blocks of life. They constitute the structural subunit of proteins, peptides, and many secondary metabolites. In addition to the 22 standard (proteinogenic) amino acids that make up the backbone of proteins, there are hundreds of other natural (non-standard) amino acids that have been discovered either in free form or as components in natural products. The amino acids used in some embodiments of the prodrugs of this invention include natural amino acids, synthetic (non-natural, unnatural) amino acids, and their derivatives.

Standard Amino Acids

There are currently 22 known standard or proteinogenic amino acids that make up the monomeric units of proteins and are encoded in the genetic code. The standard amino acids include alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine and valine. These standard amino acids have the general structure shown in FIG. 9, where R represents the side chain on the α-carbon.

Non-Standard Amino Acids

Figure 10:
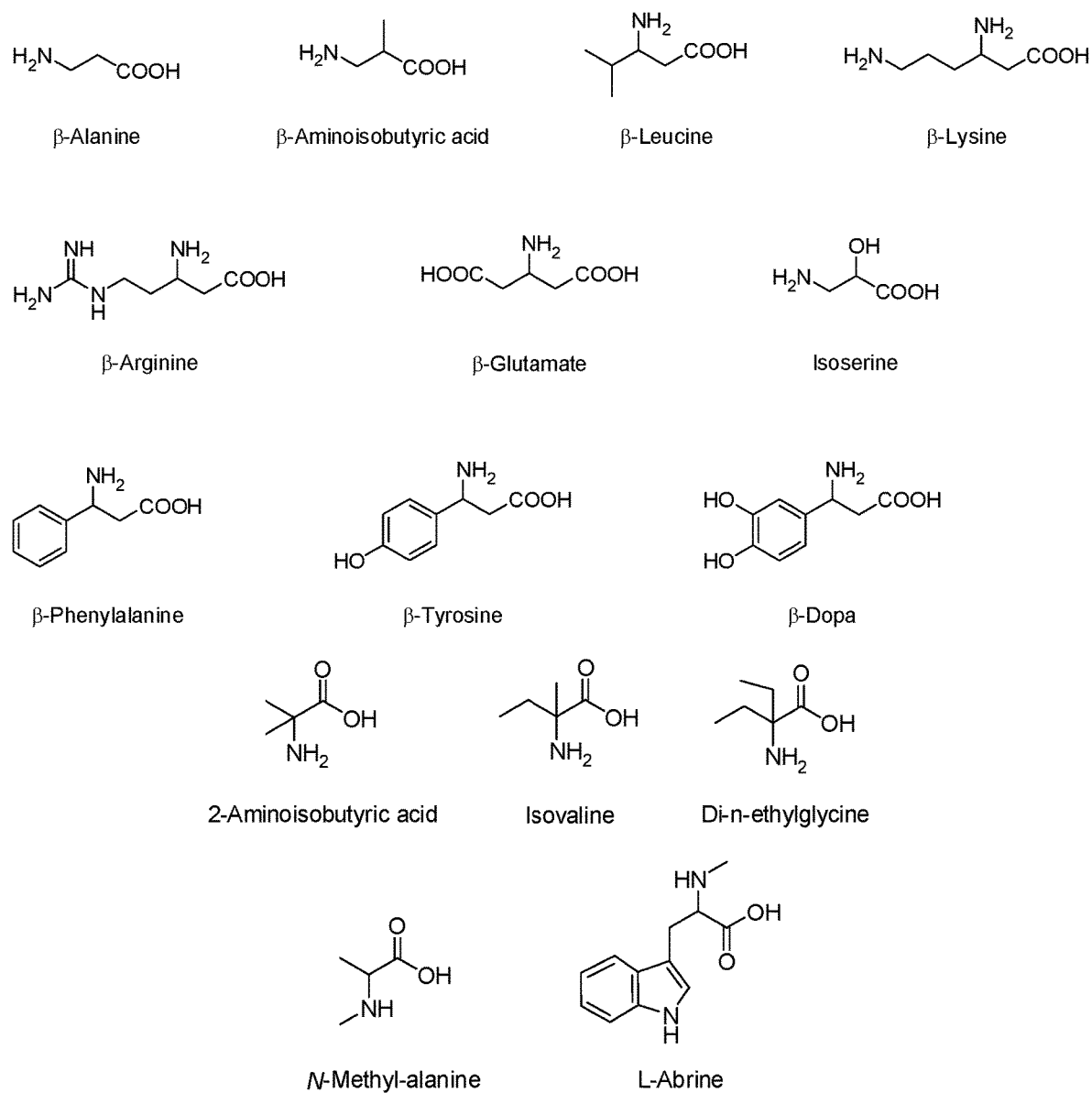
FIG. 10. Chemical structures of some non-standard amino acids for use in the making of the conjugates of the present technology.

Non-standard amino acids can be found in proteins created by chemical modifications of standard amino acids already incorporated in the proteins. This group also includes amino acids that are not found in proteins but are still present in living organisms either in their free form or bound to other molecular entities. Non-standard amino acids occur mostly as intermediates in metabolic pathways of standard amino acids and are not encoded by the genetic code. Examples of non-standard amino acids include but are not limited to ornithine, homoarginine, citrulline, homocitrulline, homoserine, theanine, γ-aminobutyric acid, 6-aminohexanoic acid, sarcosine, cartinine, 2-aminoadipic acid, pantothenic acid, taurine, hypotaurine, lanthionine, thiocysteine, cystathionine, homocysteine, β-amino acids such as β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), α,α-disubstituted amino acids such as 2-aminoisobutyric acid, isovaline, di-n-ethylglycine, N-methyl acids such as N-methyl-alanine, L-abrine, hydroxy-amino acids such as 4-hydroxyproline, 5-hydroxylysine, 3-hydroxyleucine, 4-hydroxyisoleucine, 5-hydroxy-L-tryptophan, cyclic amino acids such as 1-aminocyclopropyl-1-carboxylic acid, azetidine-2-carboxylic acid and pipecolic acid. Some structures of suitable non-standard amino acids that can be used in some embodiments of the prodrugs of this invention are shown in FIG. 10.

Synthetic Amino Acids

Synthetic amino acids do not occur in nature and are prepared synthetically. Examples include but are not limited to allylglycine, cyclohexylglycine, N-(4-hydroxyphenyl) glycine, N-(chloroacetyl)glycline ester, 2-(trifluoromethyl)-phenylalanine, 4-(hydroxymethyl)-phenylalanine, 4-amino-phenylalanine, 2-chlorophenylglycine, 3-guanidino propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, isoserine, 3-aminopentanoic acid, 2-amino-octanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-diaminopropionic acid, 5-aminovaleric acid, and 4-(dimethylamino)cinnamic acid. Some structures of suitable synthetic amino acids that can be used in some embodiments of the prodrugs of this invention are shown in FIG. 11.

Polyethylene Glycols

In some embodiments of the present technology, levorphanol, derivatives thereof or combinations thereof, is conjugated to a polyethylene glycol, or derivatives thereof. In some embodiments, the terminal hydroxyl group of the polyethylene glycol can be substituted with an amino, azide, or methoxy group. Some suitable structures of polyethylene glycols include the following:

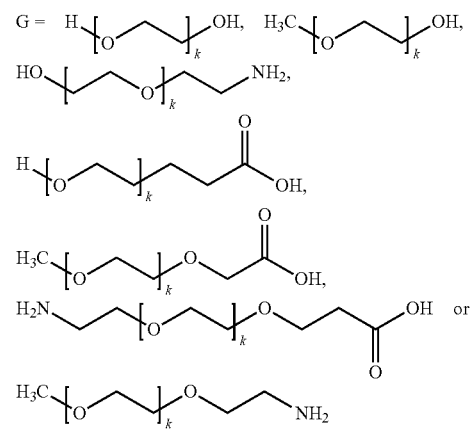

wherein k is 1-20 for these structures.

Vitamin Compounds

In some embodiments of the present technology, levorphanol, derivatives thereof, or combinations thereof, is conjugated to one or more vitamin compounds. The vitamin compounds include both water soluble and fat soluble vitamins or derivatives thereof. Useful vitamin compounds are those that have one or more carboxylic acid groups, one or more hydroxyl groups, or one or more other reactive functional groups that can form a bond with levorphanol either directly or through one or more linkers. Examples of water soluble vitamins that could be conjugated to levorphanol include biotin, folate (folic acid), niacin, pantothenic acid, riboflavin, thiamin, pyridoxine, and ascorbic acid. Examples of fat soluble vitamins that could be conjugated to levorphanol include Vitamin A (retinol), vitamin $D_2$ (ergocalciferol), vitamin $D_3$ (cholecalciferol), vitamin E (tocopherols and tocotrienols, including alpha, beta, gamma, and delta-tocopherol), and vitamin K (phylloquinone). Some structures of suitable water soluble vitamins and fat soluble vitamins for use in the present technology are found in FIGS. 12A and 12B, respectively.

Linkers

In some embodiments of the present technology, the levorphanol, derivatives thereof, or combinations thereof, is conjugated to one or more organic oxoacids, amino acids, polyethylene glycols, or vitamin compounds via one or more linkers. Linker moieties of the present technology, which connect the one or more organic oxoacids, amino acids, polyethylene glycols, or vitamin compounds to the levorphanol, derivatives thereof or combinations thereof, can have the following general formulas:

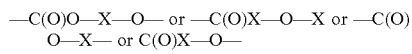
—C(O)O—X—O— or —C(O)X—O—X or —C(O)O—X— or C(O)X—O— for conjugation at the C-3 hydroxyl position;

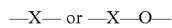
—X— or —X—O— for conjugation at the N-17 tertiary amine position;
wherein X in these linker formulas is selected from a representative group including alkyl, substituted alkyl, aryl, substituted aryl, arylalkyl, substituted alkylaryl, heteroalkyl, substituted heteroalkyl, heteroaryl, substituted heteroaryl, heterocycle, substituted heterocycle, alkenyl, substituted alkenyl, alkynyl, substituted alkynyl, cycloalkyl, substituted cycloalkyl, cycloalkenyl, substituted cycloalkenyl, cycloalkynyl, or substituted cycloalkynyl.

Preferred embodiments of the present technology include linkers where X is at least one aliphatic group. More preferred embodiments include linkers where X is at least one alkyl group.

Physiological Benefits

The above defined prodrugs or conjugates of levorphanol can be given orally and, upon administration, release the active levorphanol after being hydrolyzed in the body. Not to be bound by any particular theory, it is believed that, since the oxoacids, polyethylene glycols, and vitamin compounds of this invention are naturally occurring metabolites or mimetics thereof or pharmaceutically active compounds, these prodrugs can be easily recognized by physiological systems resulting in hydrolysis and release of levorphanol. The claimed prodrugs themselves are either not active or have limited pharmacological activity and consequently may follow a metabolic pathway that differs from the parent drug. By choosing suitable oxoacids, polyethylene glycols, and/or vitamin compounds ("ligands"), the release of levorphanol into the systemic circulation can be controlled even when the prodrug is administered via routes other than oral. In one embodiment, the modified or conjugated levorphanol would release levorphanol similar to free or unmodified or unconjugated levorphanol. In another embodiment, the modified or conjugated levorphanol may have a more rapid release of levorphanol compared to unmodified or unconjugated levorphanol. In another embodiment, the modified levorphanol would be released in a controlled or sustained manner. This controlled release can potentially alleviate certain side-effects and improve upon the safety profile of the parent drug. These side-effects may include, dizziness, lightheadedness, drowsiness, nausea, vomiting, constipation, stomach pain, rash, difficulty urinating, difficulty breathing and fainting. In addition, levorphanol and other opioids (opiates) are also highly addictive and prone to substance abuse.

Recreational drug abuse of opioids is a common problem and usually begins with oral doses taken with the purpose of achieving euphoria ("rush", "high"). Over time the drug abuser often increases the oral dosages to attain more powerful "highs" or to compensate for heightened opioid tolerance. Rapid metabolism and fast duration of action of levorphanol, contributes to its likelihood of being abused. This behavior can escalate and result in exploring other routes of administration such as intranasal ("snorting") and intravenous ("shooting"). In some embodiments, levorphanol that is conjugated with a suitable ligand does not result in rapid spikes in plasma concentrations after oral administration that is sought by a potential drug abuser. In some embodiments, levorphanol released from the conjugate may have a delayed $T_{max}$ and possibly lower $C_{max}$ than the parent drug. Not to be bound by any particular theory, it is believed that the conjugates of the present technology, when taken orally or by other non-oral routes, reduce, lessen, or do not provide the feeling of a "rush" when taken orally even at higher doses, but still maintain pain relief. In another embodiment, levorphanol conjugated with appropriate ligands of this invention is not hydrolyzed efficiently when administered via non-oral routes. As a result, in some embodiments, the prodrugs of the present technology do not generate as high plasma or blood concentrations of released levorphanol when injected or snorted compared to free levorphanol administered through these routes.

In some embodiments, the conjugates of the present technology, since they comprise ligands covalently bound to levorphanol, are not able to be physically manipulated to release the levorphanol from the conjugated levorphanol by methods, for example, of grinding up or crushing of solid forms.

Opioid induced constipation is a common side effect of pain treatment with opioids. It affects approximately 40-90% of the patients who are chronically taking opioid medication. Additionally, patients suffering from OIC may become resistant to laxative treatments. Although the mechanism is not yet fully understood, it is assumed that the binding of agonists to the peripheral μ-opioid receptors in the gastrointestinal (GI) tract is the primary cause of OIC. This opioid receptor activation impairs the coordination of the GI function by the enteric nervous system (ENS) resulting in decreased gut motility by delaying the transit time of fecal content through interference with the normal tone and contractility of the bowels. While the contractions of the circular muscles are increased causing non-propulsive kneading and churning (stasis) and increased fluid absorption, the longitudinal smooth muscle tone is decreased causing reduced forward peristalsis and additional time for desiccating fecal matter. Furthermore, the anal sphincter tone is increased making defecation more difficult. The clinical presentation of these effects typically manifests itself in symptoms of hard/dry stool, straining, incomplete evacuation, bloating and abdominal distention.

In one embodiment, the prodrugs of this invention have no or insignificant activity at the μ-opioid receptors. In another embodiment, they are not subjected to enzymatic hydrolysis until they are absorbed in the gut. Consequently, the active levorphanol is effectively "cloaked" by the attached ligand and may bypass the peripheral μ-opioid receptors without affecting the ENS thereby reducing or preventing OIC.

The at least one prodrug or conjugate of the present technology can be formulated into dosage forms that include but are not limited to tablet, capsule, caplet, troche, lozenge, powder, suspension, syrup, solution, oral thin film (OTF), oral strips, inhalation compounds, suppositories, or transdermal patches. In some embodiments, the dosage forms are administered orally. Preferred oral administration forms are solutions, syrups, suspensions, capsules, tablets and OTF. Suitable dosing vehicles of the present technology include, but are not limited to, water, phosphate buffered saline (PBS), Tween in water, and PEG in water.

Solid dosage forms can optionally include one or more of the following types of excipients: antiadherents, binders, coatings, disintegrants, gel-forming agents, fillers, flavors and colors, glidants, lubricants, preservatives, sorbents and sweeteners, among others.

Oral formulations of the present technology can also be included in a solution, a suspension or a slurry, in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The individual units so formed are then dried to constant weight.

Chewable tablets, for example, may be prepared by mixing the formulations with excipients designed to form a relatively soft, flavored, tablet dosage form that is intended to be chewed rather than swallowed. Conventional tablet machinery and procedures, for example, direct compression and granulation, i.e., or slugging, before compression, can be utilized. Those individuals involved in pharmaceutical solid dosage form production are versed in the processes and the machinery used, as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with one or more excipients intended to add binding qualities to disintegration qualities. The mixture is either directly compressed, or granulated and then compressed using methods and machinery known to those in the industry. The resultant compressed tablet dosage units are then packaged according to market need, for example, in unit dose, rolls, bulk bottles, blister packs, etc.

The present technology contemplates that the conjugates of the present technology can be formulated into formulations or co-formulations that may further comprise one or more additional components. For example, such formulations can include biologically-acceptable carriers which may be prepared from a wide range of materials. Without being limited to, such materials include diluents, binders and adhesives, lubricants, gel-forming agents, plasticizers, disintegrants, surfactants, colorants, bulking substances, flavorings, sweeteners and miscellaneous materials such as buffers and adsorbents in order to prepare a particular medicated formulation.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons working in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

It should be understood that in addition to the ingredients particularly mentioned above, the formulations of the present technology can include other suitable agents such as flavoring agents, preservatives and antioxidants. Such antioxidants would be food acceptable and could include vitamin E, carotene, BHT or other antioxidants.

Other compounds which may be included by admixture are, for example, medically inert ingredients, e.g., solid and liquid diluents, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulfates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular, a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol. The ingredients mentioned herein are not intended to be exhaustive, and one of skill in the art will be able to formulate compositions using known or to be known ingredients.

It is contemplated that the levorphanol conjugates of the present technology can be combined with one or more active substances, such as different levorphanol conjugates, unconjugated levorphanol, narcotic and/or non-narcotic active ingredients, depending on intended indication. Examples of active pharmaceuticals that can be combined with the conjugates of the present technology include, but are not limited to, acetaminophen, phenylpropanolamine, ibuprofen, aspirin, toradol, ketorolac, diclofenac, pheniramine, chlorpheniramine, phenylephrine, pseudoephedrine, pyrilamine, dexyalamine, guaifenesin, codeine, oxycodone, oxymorphone, hydrocodone, hydromorphone, methadone, morphine, fentanyl, benzodiazepines, carbamezine, prochlorperazine, piperazines, piperazine derivatives, dextrorphan, dextromethorphan, magnesium salicylate, magnesium sulfate, and endothelin antagonists. The conjugated levorphanol of the present technology can be formulated with one or a combination of these or other active substances or as a standalone active ingredient without any other actives.

The amounts and relative percentages of the different active and inactive components of the formulations of the current technology can be modified, selected and adjusted in order to arrive at desirable formulations, dosages and dosage forms for therapeutic administration of the compounds, products, compositions, conjugates and prodrugs of the current technology.

The compositions comprising the levorphanol conjugates or prodrugs may be used in methods of treating a patient having a disease, disorder or condition requiring or mediated by binding of an opioid to the opioid receptors and/or by binding of an NMDA receptor antagonist to the NMDA receptors of the patient. In some embodiments, the conjugate prodrugs or compositions of the present technology may be administered for the relief or treatment of pain, including acute, chronic, nociceptive, neuropathic, central, and/or peripheral pain.

In further embodiments, compositions comprising the levorphanol conjugates of the present technology may be used as an anesthetic, or for the treatment of such conditions as hyperalgesia, Alzheimer's disease, pseudobulbar affect (PBA), and post-traumatic stress disorder (PTSD). In certain embodiments, the compositions comprising the levorphanol conjugates of the present technology may be used in combination with quinidine for the treatment of PBA and/or PTSD. In other embodiments, compositions of the present technology may potentiate the effects of certain opioids, such as for example oxycodone, in suppressing neuropathic pain, thus potentially permitting a lower dose of oxycodone to be administered to a patient and thereby decreasing side effects of oxycodone treatment of neuropathic pain in said patient.

Not to be bound by any one theory it is believed that the central glutaminergic system is involved in the transmission and modulation of pain signals. Prolonged binding of opioids to opioid receptors leads in part to pathological activation of NMDA receptors, an ionotropic glutamate receptor, and increase in NMDA calcium channels. The activated NMDA receptor facilitates the inward flow of calcium which in turn activates opioid receptor phosphorylation by protein kinase C. This phosphorylation inactivates the opioid receptor resulting in opioid tolerance and in central sensitization accompanied by enhanced nociception. The latter may manifest opioid-induced hyperalgesia (OIH) in the patient.

Through similar mechanisms, sustained and repeated NMDA receptor activation caused by, for example, upregulation of glutamate transporters and the associated reduction in glutamate uptake following nerve damage can lead to neuropathic pain.

Blocking the NMDA receptor by NMDA receptor antagonists such as levorphanol may disrupt the glutaminergic pathways, and thus provide relief for OIH and reduce opioid tolerance. As a result, levorphanol may be suitable for opioid rotation. Switching opioid therapy from, for example, oxycodone or morphine to levorphanol may improve patient analgesia through its unique opioid receptor activity profile as well as through blocking of NMDA receptors. In addition, blockage of the NMDA receptor by levorphanol may treat neuropathic pain by modulating the action of glutamate in the glutaminergic transmission of nociceptive signals.

Treatment of a patient comprises orally administering to the patient a pharmaceutically effective amount of at least one conjugate of levorphanol as described in the present technology. The patient may be a human or animal patient. As used herein, the term animal is used in the veterinary sense and does not include humans. Human patients who may be treated include neonatal patients, pediatric patients, adolescent patients, adult patients, geriatric patients, elderly patients, and normative patients. In some embodiments, the conjugate can exhibit a lower, equivalent, or higher AUC when compared to an equivalent molar amount of unconjugated levorphanol, and can exhibit a slower, similar, or faster rate of release. In other embodiments, at least one conjugate can exhibit less variability in the oral PK profile when compared to unconjugated levorphanol.

Dosing of the prodrugs or compositions will be dependent on the age and body weight of the patient, and the severity of the symptoms to be treated. In some embodiments, dosages of the levorphanol conjugate of the present technology include, but are not limited to, formulations including from about 0.1 mg or higher, alternatively about 0.5 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher of the levorphanol conjugate, and include any additional increments thereof, for example, 0.1, 0.2, 0.25, 0.3, 0.4, 0.5, 0.6, 0.7, 0.75, 0.8, 0.9 or 1.0 mg and multiplied factors thereof, (e.g., ×1, ×2, ×2.5, ×5, ×10, ×100, etc).

In some embodiments, compositions comprising the levorphanol conjugates of the present technology could be orally administered at a dosing regimen of one time a day, alternatively two times a day, alternatively four times a day. In some embodiments, doses of the composition comprising the levorphanol conjugate could be administered at 1 dose every 4 to 6 hours, alternatively 1 to 2 doses every 4 to 6 hours, alternatively 6 to 8 hours, alternatively 6 doses in a 24 hour period.

In some embodiments, compositions comprising the levorphanol conjugates of the present technology could be administered for a period of about 3 days, alternatively about 5 days, alternatively about 7 days, alternatively about 10 days, alternatively about 12 days, alternatively about 14 days, alternatively about 21 days, alternatively about 30 days, alternatively about 60 days, alternatively about 90 days, or alternatively about 120 days, among others. It should also be appreciated by those skilled in the art that, in some embodiments, rotational dosing utilizing one or more compositions of the present technology, or rotational dosing wherein one or more compositions of the present technology are used in conjunction with one or more opioids, such as, for example hydrocodone, hydromorphone, oxycodone, or oxymorphone, or conjugates of one or more opioids, is also envisaged.

Pharmaceutical Kits

In some embodiments, the present technology provides pharmaceutical kits comprising a levorphanol prodrug or composition of the present technology. In some embodiments, a specific amount of individual doses in a package contain a pharmaceutically and/or therapeutically effective amount of the levorphanol prodrug or conjugate of the present technology. In some embodiments, the kit comprises one or more blister packs containing the prodrug or composition of the present technology.

The kit can further include instructions for use of the kit. In some embodiments, the instructions for use are for the treatment of pain in a neonatal, pediatric, adolescent, adult, normative, or geriatric patient. In other embodiments, the instructions for use are for the treatment of any of the diseases, disorders, conditions, or syndromes identified above. The specified amount of individual doses may contain from about 1 to about 100 individual dosages, alternatively from about 1 to about 60 individual dosages, alternatively from about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, about 1, about 2, about 5, about 10 and multiplied factors thereof, (e.g., about ×1, about ×2, about ×2.5, about ×5, about ×10, about ×100, etc.).

Synthetic Schemes

The present technology also provides methods of synthesis for the preparation of the levorphanol conjugates of the present technology. In some embodiments, one or more protecting groups may be attached to any additional reactive functional groups that may interfere with the coupling to levorphanol. Any suitable protecting group may be used depending on the type of functional group and reaction conditions. Some protecting group suitable for use in the present technology include, but are not limited to, acetyl (Ac), tert-butyoxycarbonyl (Boc), benzyloxycarbonyl (Cbz), p-methoxybenzylcarbonyl (Moz), 9-fluorenylmethyloxycarbonyl (Fmoc), benzyl (Bn), p-methoxybenzyl (PMB), 3,4 dimethoxybenzyl (DMPM), p-methozyphenyl (PMP), tosyl (Ts), or amides (like acetamides, pthalamides, and the like).

In other embodiments, a base may be required at any step in the synthetic scheme of prodrugs of levorphanol of this invention. Suitable bases include, but are not limited to, 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert.-butoxide (e.g., potassium tert.-butoxide), any alkali metal hydride (e.g., sodium hydride), any alkali metal alkoxide (e.g., sodium methoxide), triethylamine or any other tertiary amine.

Suitable solvents that can be used for any reaction at any step in the synthetic scheme of a prodrug of levorphanol of this invention include, but are not limited to, acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert.-butyl ether (MTBE), isopropanol, isopropyl acetate, diisopropyl ether, tetrahydrofuran, toluene, xylene or water.

In some embodiments, an acid may be used to remove certain protecting groups. Suitable acids include, but are not limited to, hydrochloric acid, hydrobromic acid, hydrofluoric acid, hydriodic acid, sulfuric acid, phosphoric acid, trifluoroacetic acid, acetic acid, citric acid, methanesulfonic acid, p-toluenesulfonic acid and nitric acid. For certain other protecting groups, a catalytic hydrogenation may be used, e.g., palladium on charcoal in the presence of hydrogen gas.

Provided herein are some reaction schemes that could be used to prepare some embodiments of the levorphanol conjugates of the present technology.

It should be understood that the general reaction schemes provided are exemplary, and that one skilled in the art can modify or tailor the reaction schemes to achieve particular outcomes, purposes, and/or advantages.

Prophetic Reaction Schemes:

Synthesis of Cbz-Val-O—CH$_2$—Cl:

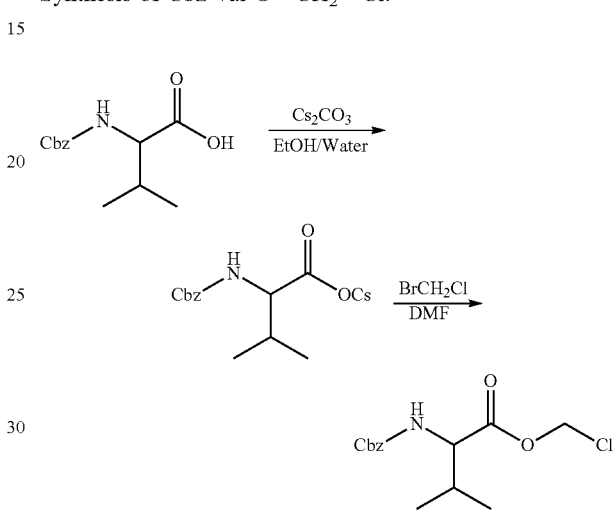

Synthesis of N-(Val-CH$_2$)-levorphanolium chloride

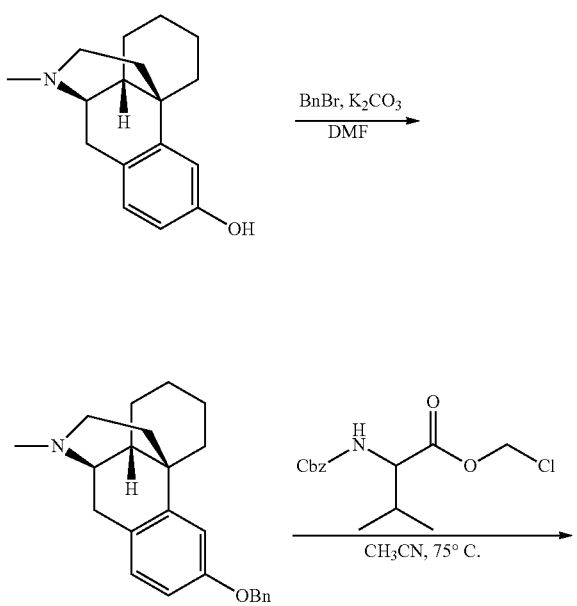

-continued
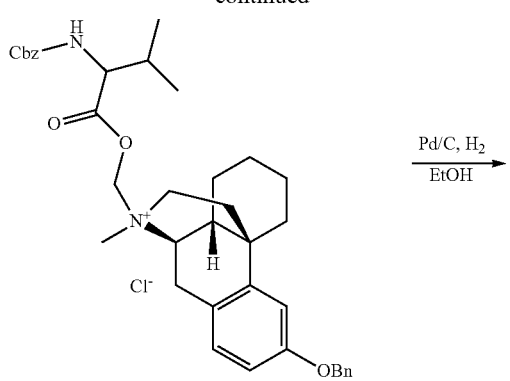
Pd/C, H₂
EtOH
→
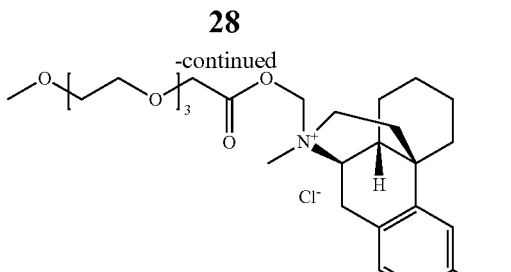
Synthesis of Boc-Ser(C(O)OCH₂Cl)—OᵗBu
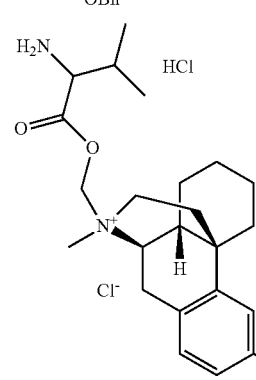
Chloromethyl chloroformate
TEA, CH₂Cl₂
→
Synthesis of N-(Ser-(C(O)OCH₂))-levorphanolium chloride
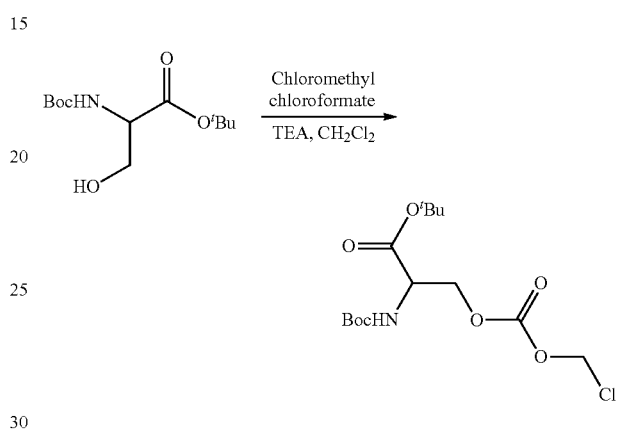
CH₃CN, 75° C.
→
Synthesis of MeO-PEG₃-CH₂C(O)OCH₂—Cl
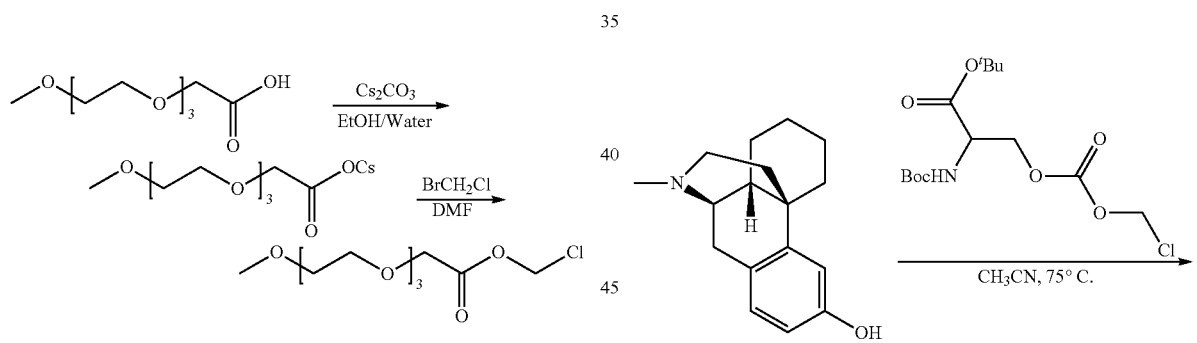
Synthesis of N-(MeO-PEG₃-CH₂C(O)OCH₂)-levorphanolium chloride
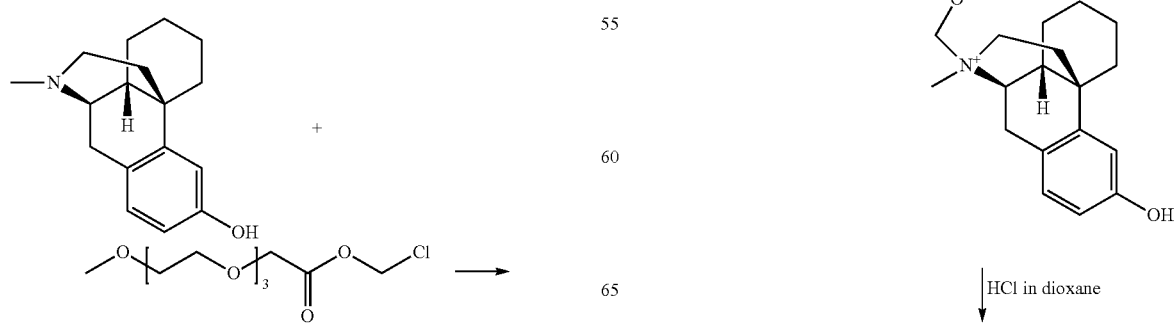
HCl in dioxane ↓

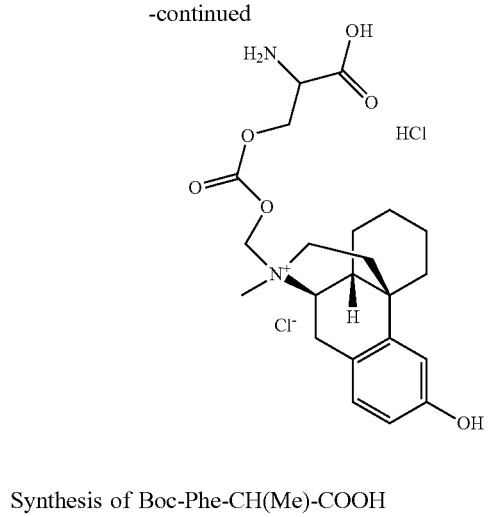
Synthesis of Boc-Phe-CH(Me)-COOH
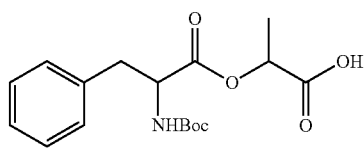
Synthesis of nicotinoyl-O—CH₂—Cl
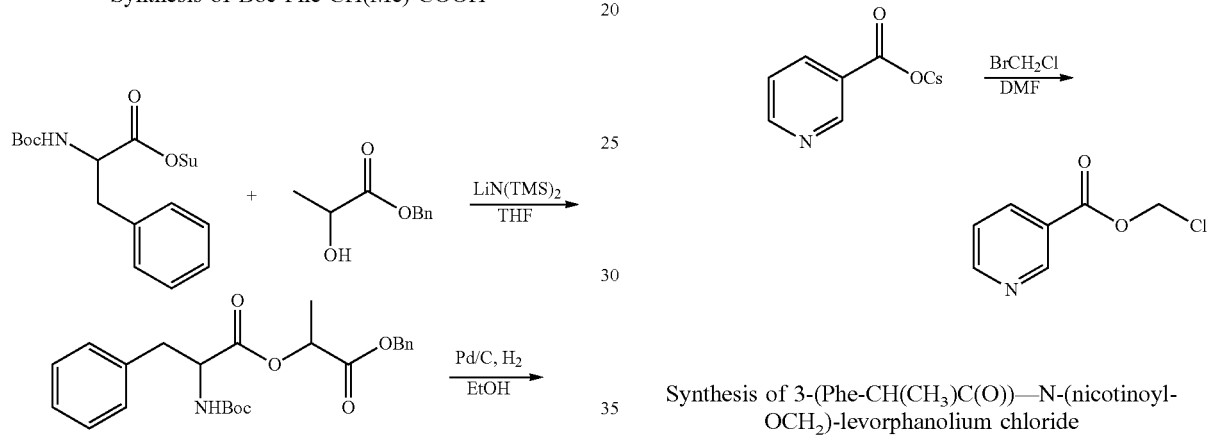
Synthesis of 3-(Phe-CH(CH₃)C(O))—N-(nicotinoyl-OCH₂)-levorphanolium chloride
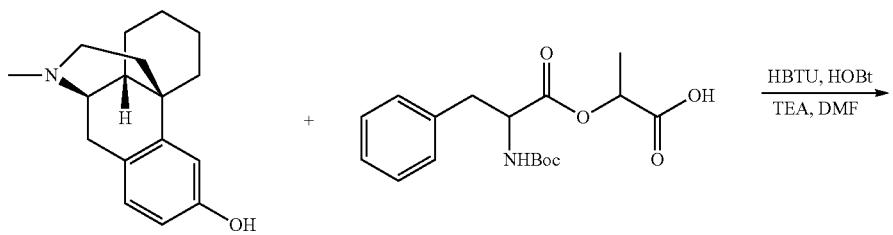
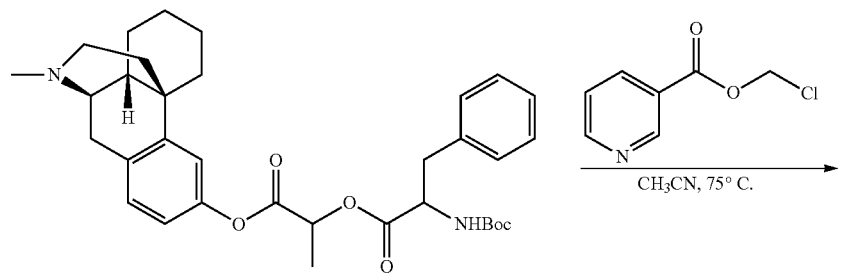

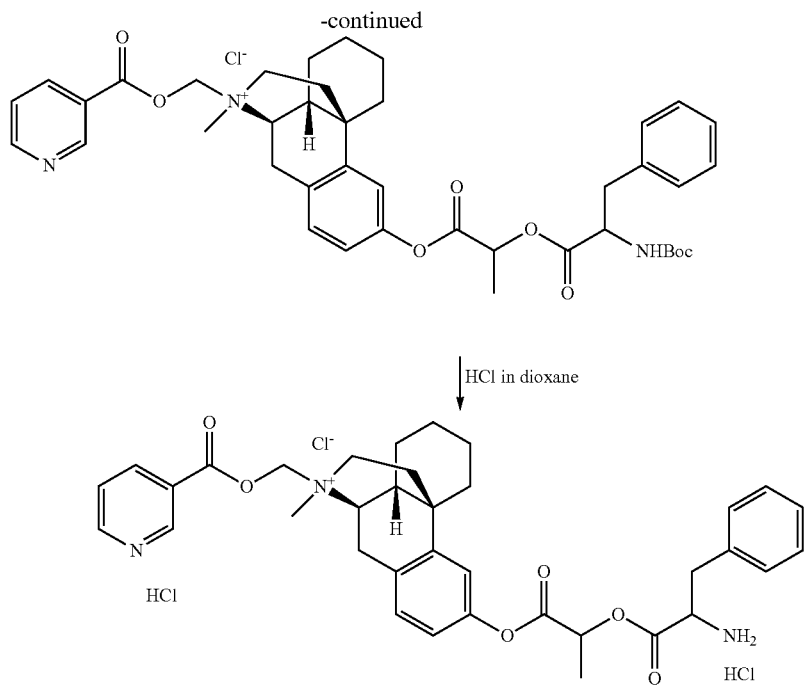

The presently described technology and its advantages will be better understood by reference to the following examples. These examples are provided to describe specific embodiments of the present technology. By providing these specific examples, it is not intended to limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

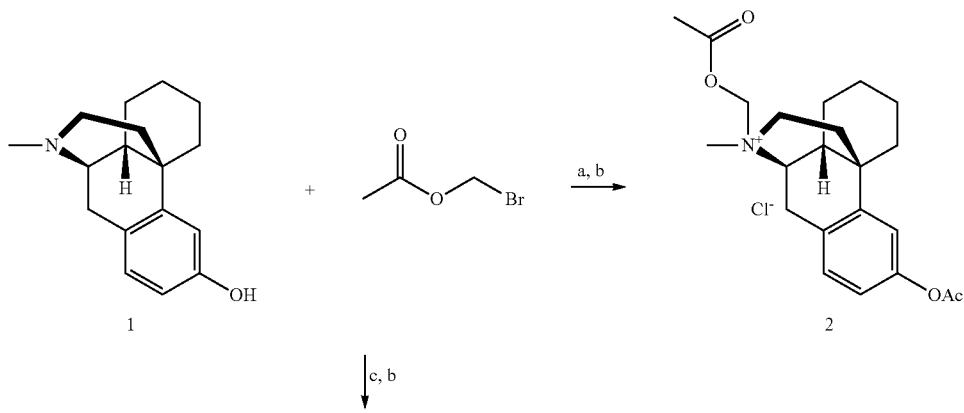

Scheme 1. (a) 1,2,2,6,6-Pentamethylpiperidine CH₃CN, 75° C.; (b) 4N HCl/dioxane; (c) CH₃CN, 75° C.

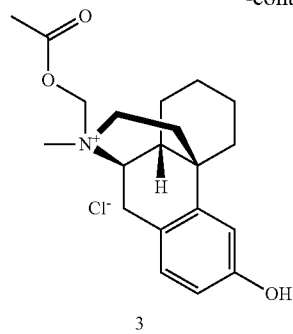

3

Example 1: Synthesis of 3-Acetyl-N-(acetyl-OCH₂)-levorphanolium 2

A solution of levorphanol 1 (0.1 g, 0.39 mmol), 1,2,2,6,6-pentamethylpiperidine (0.1 mL, 0.6 mmol) and acetyloxymethyl bromide (0.061 mL, 0.6 mmol) in CH₃CN was heated at 75° C. for 2 hours. Solvent was evaporated under reduced pressure and the residue was purified by preparative HPLC. The purified quaternary salt was dissolved in 4N HCl in dioxane and stirred at room temperature for 20 min. The solvent was evaporated, the residue was co-evaporated with IPAc and dried to give the chloride salt 2 (0.028 g, 18%).

Example 2: Synthesis of N-(Acetyl-OCH₂)-levorphanolium 3

A solution of levorphanol 1 (0.1 g, 0.39 mmol) and acetyloxymethyl bromide (0.061 mL, 0.6 mmol) in CH₃CN (8 mL) was heated at 75° C. for 2 hours. Solvent was evaporated under reduced pressure and the residue was purified by preparative HPLC. The purified quaternary salt was dissolved in 4N HCl in dioxane and stirred at room temperature for 20 minutes. The solvent was evaporated, the residue was co-evaporated with IPAc and dried to give the chloride salt 3 (0.052 g, 36%).

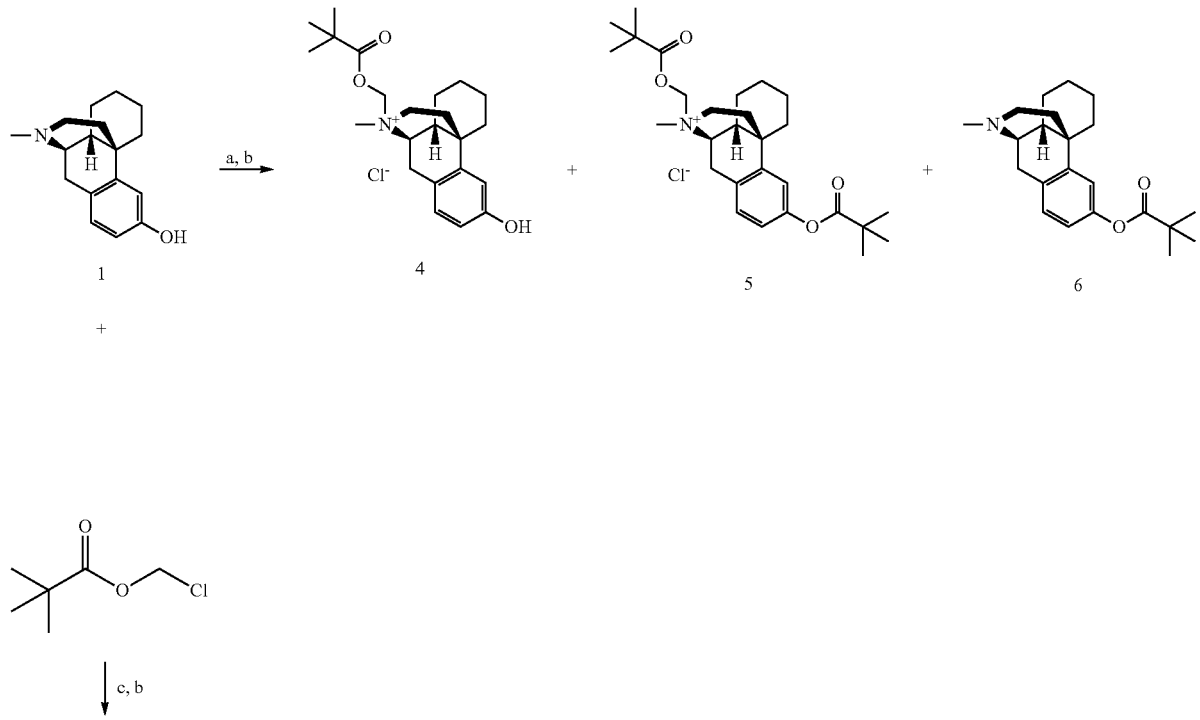

Scheme 2. (a) CH₃CN, 75° C.; (b) Dowex 1 × 4 chloride, water/CH₃CN; (c) 1,2,2,6,6-Pentamethylpiperidine CH₃CN, 75° C.

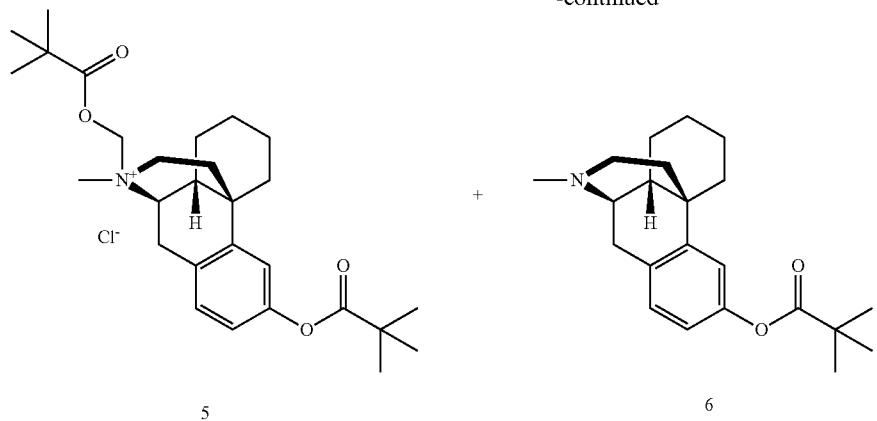

Example 3: Synthesis of N-(Pivaloyl-OCH₂)-levorphanolium 4,3-pivaloyl-N-(pivaloyl-OCH₂)-levorphanolium chloride 5 and 3-pivaloyl-levorphanol 6

A suspension of levorphanol 1 (0.22 g, 0.85 mmol) and chloromethyl pivalate (0.19 mL, 1.27 mmol) in CH₃CN (12 mL) was heated at 75° C. for 12 hours. Additional chloromethyl pivalate (0.095 mL, 0.6 mmol) was added and heating was continued at 75° C. for additional 6 hours. Solvent was evaporated under reduced pressure and the mixture of products was separated by preparative HPLC. The quaternary salts, after separation, were treated with dowex 1×4 chloride form (water:CH₃CN=1:1), filtered and the filtrate was lyophilized to afford compound 4 (0.065 g, 19%) and compound 5 (0.072 g, 17%) as white solid. In addition, 3-monosubstituted levorphanol conjugate 6 formed as minor product during the reaction.

Example 4: Alternative Synthesis of 3-pivaloyl-N-(pivaloyl-OCH₂)-levorphanolium chloride 5 and 3-pivaloyl-levorphanol 6

A mixture of levorphanol 1 (0.13 g, 0.5 mmol), 1,2,2,6,6-pentamethyl piperidine (0.136 mL, 0.75 mmol) and chloromethyl pivalate (0.11 mL, 0.75 mmol) in CH₃CN (8 mL) was heated at 75° C. for 8 hours. Additional chloromethyl pivalate (0.11 mL, 0.75 mmol) was added and heating was continued for additional 10 hours. Solvent was evaporated under reduced pressure and the mixture of products were separated by preparative HPLC. The quaternary salt was treated with dowex 1×4 chloride form (water/CH₃CN) and lyophilized to give compound 5 (0.125 g, 51%) as white powder. In addition, 3-monosubstituted levorphanol conjugate 6 formed as minor product during the reaction.

Scheme 3. (a) 1,2,2,6,6-Pentamethylpiperidine CH₃CN, 75° C.; (b) Dowex 1 × 4 chloride, water/CH₃CN

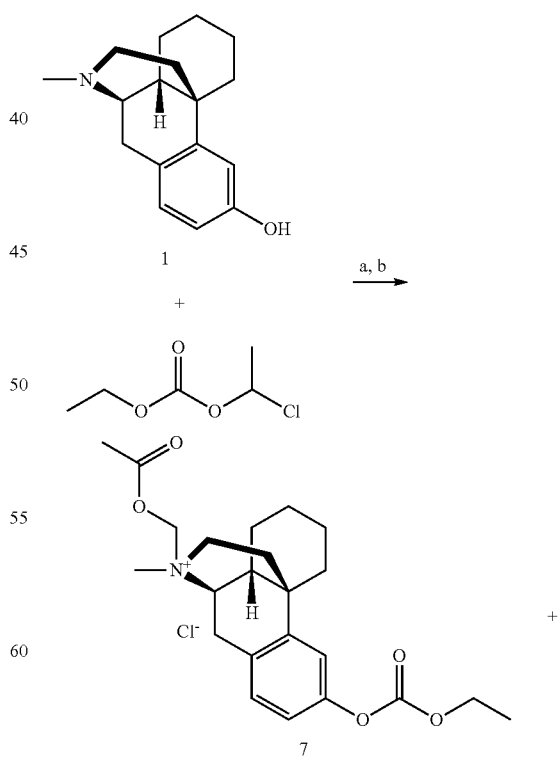

-continued

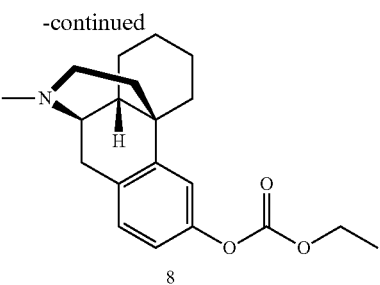

8

Example 5: Synthesis of 3-(ethoxy-C(O))—N-(ethoxy-C(O)CH(CH₃))-levorphanolium chloride 7 and 3-(ethoxy-C(O))-levorphanol 8

A mixture of levorphanol 1 (0.13 g, 0.5 mmol), 1-chloroethyl ethyl carbonate (0.135 mL, 1 mmol), 1,2,2,6,6-pentamethylpiperidine (0.135 mL, 0.75 mmol) and NaI (0.15 g, 1 mmol) in $CH_3CN$ (8 mL) was heated at 75° C. for 8 hours. Solvent was evaporated under reduced pressure and the mixture of products were separated by preparative HPLC. The quaternary salt was treated with Dowex 1×4 chloride form (water/$CH_3CN$), filtered and the filtrate was lyophilized to give compound 7 (0.035 g, 14%). In addition, 3-monosubstituted levorphanol conjugate 8 formed as minor product during the reaction.

Figure 13:
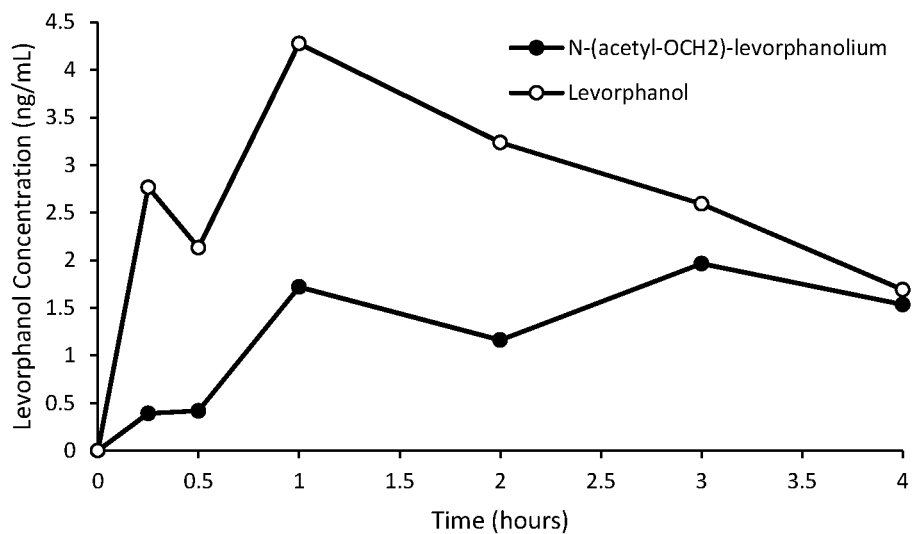
FIG. 13. Oral PK curves comparing N-(acetyl-$OCH_2$)-levorphanolium conjugate with unconjugated levorphanol in rats.
Figure 14:
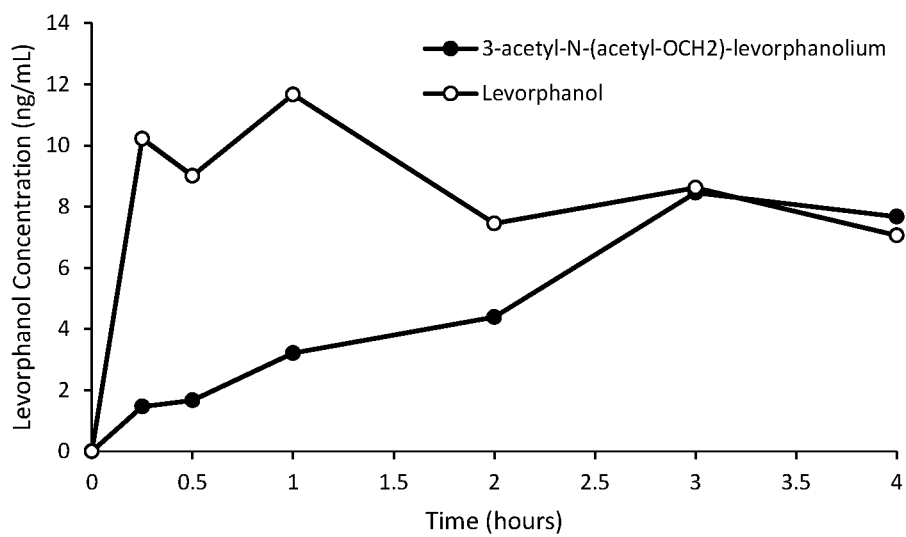
FIG. 14. Oral PK curves comparing 3-acetyl-N-(acetyl-$OCH_2$)-levorphanolium conjugate with unconjugated levorphanol in rats.

Example 6: Comparison of Oral PK Profiles of Conjugates of Levorphanol in Rats Conjugates of levorphanol and levorphanol tartrate comparator compound were dissolved in an appropriate vehicle and administered in rats via oral gavage. A summary of the doses and vehicles used for each compound is provided in Table 1 below. Whole blood samples were collected via retro-orbital bleeding at 0.25, 0.5, 1, 2, 3, 4, and optionally at 6 hours postdose. Blood samples were centrifuged and the resulting plasma samples were collected for analysis of levorphanol concentrations by LC-MS/MS. PK profiles comparing the plasma concentrations of levorphanol released from the conjugates and from the levorphanol tartrate comparator are shown in FIGS. 13 and 14.

TABLE 1

| Conjugate | Conjugate Dose (mg/kg) | Comparator[a] Dose (mg/kg) | Vehicle[b] | ROA[c] |
|---|---|---|---|---|
| N-(acetyl-OCH₂)-levorphanolium Cl | 5.39 | 6.00 | Water | Oral |
| 3-acetyl-N-(acetyl-OCH₂)-levorphanolium Cl | 6.01 | 6.00 | Water | Oral |
| N-(acetyl-OCH₂)-levorphanolium Cl | 0.18 | 0.20 | Water | Intranasal |
| 3-acetyl-N-(acetyl-OCH₂)-levorphanolium Cl | 0.20 | 0.20 | Water | Intranasal |

[a] comparator = levorphanol tartrate; the comparator and conjugate doses are equimolar
[b] the same vehicle was used for conjugate and comparator
[b] ROA = route of administration

Figure 15:
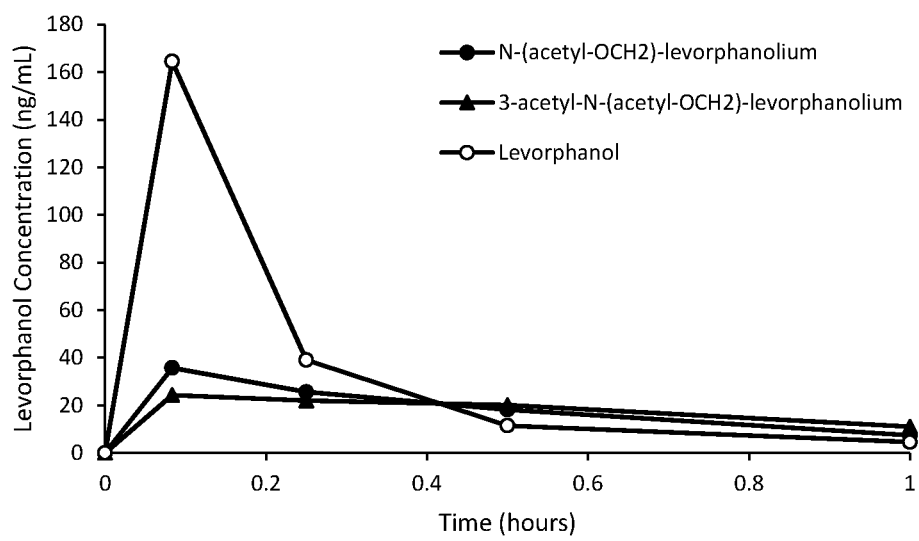
FIG. 15. Intranasal PK curves comparing N-(acetyl-$OCH_2$)-levorphanolium conjugate and 3-acetyl-N-(acetyl-$OCH_2$)-levorphanolium conjugate with unconjugated levorphanol in rats.

Example 7: Comparison of Intranasal PK Profiles of Conjugates of Levorphanol in Rats N-(acetyl-OCH₂)-levorphanolium chloride conjugate, 3-acetyl-N-(acetyl-OCH₂)-levorphanolium chloride conjugate, and levorphanol tartrate comparator compound were dissolved in an appropriate vehicle and administered in rats by slowly adding the respective dosing solution drop-wise and alternating into the nasal openings. A summary of the doses and vehicles used for each compound is provided in Table 1 above. Whole blood samples were collected via retro-orbital bleeding at 5 minutes and at 0.25, 0.5, and 1 hours postdose. Blood samples were centrifuged and the resulting plasma samples were collected for analysis of levorphanol concentrations by LC-MS/MS. PK profiles comparing the plasma concentrations of levorphanol released from the conjugates and from the levorphanol tartrate comparator are shown in FIG. 15.

In the present specification, use of the singular includes the plural except where specifically indicated.

The compounds, compositions, and methods described herein can be illustrated by the following embodiments enumerated in the numbered paragraphs that follow:

1. A compound or composition comprising at least one conjugate of levorphanol having the following general formula:

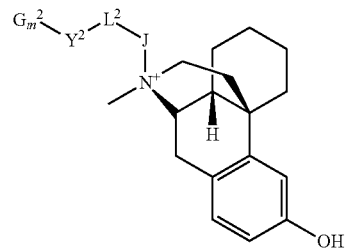

where $L^2$ is absent, or is

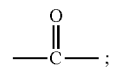

$Y^2$ is absent, or $[A-X-Z]_n$
where A, X, Z are independently absent or selected from —O—, —S— or —$(CR^1R^2)_k$—
J is $[M-W]_p$
where M is absent or —$(CR^3R^4)_q$—; and W is absent, or —O— or —S—
$R^1$, $R^2$, $R^3$, $R^4$ are each independently selected from H, alkyl, aryl, alkyl aryl, alkoxy, haloalkyl, or haloaryl
n and k are independently 1-4
p and q are independently 1-4
$G_m^2$ is absent or selected independently for each repeating subunit from H, oxoacid, polyethylene glycol having from 2 to 5 ethylene oxide units, or a vitamin compound, and m is 1-4, except m is 1 when G is H;
or a pharmaceutically acceptable salt thereof.

2. The compound or composition of Paragraph 1, wherein M is —$(CR^3R^4)_q$—; W, $L^2$ and $Y^2$ are absent; $G^2$ is at least one oxoacid; and m is 1-3.

3. The compound or composition of Paragraph 2, wherein $R^3$ is H; $R^4$ is H, methyl or phenyl; and p is 1.

4. The compound or composition of Paragraph 1, wherein M is —$(CR^3R^4)_q$—, W is —O—, L is present, A is O and X is —$(CR^1R^2)_k$—, $G^2$ is at least one oxoacid and m is 1-3.

5. The compound or composition of Paragraph 4, wherein $R^1$, $R^2$ and $R^3$ are H; $R^4$ is H, methyl or phenyl; q is 1; and k is 1 to 4.

6. A compound or composition comprising at least one conjugate of levorphanol having the following general formula:

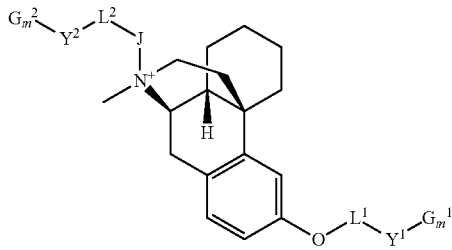

where L¹ and L² are independently absent, or

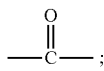

Y¹ and Y² are independently either absent, or [A-X—Z]$_n$
where A, X, Z are independently selected for Y¹ and Y², and are independent of each other either absent or selected from the group of —O—, —S—, or —(CR¹R²)$_k$—
J is [M-W]$_p$
where M is absent or —(CR³R⁴)$_q$—; and W is absent, or —O— or —S—
R¹, and R², are each independently selected for Y¹ and Y², and are, independent of each other, selected from H, alkyl, aryl, alkyl aryl, alkoxy, haloalkyl, or haloaryl
R³ and R⁴ are each independently selected from H, alkyl, aryl, alkyl aryl, alkoxy, haloalkyl, or haloaryl
for each Y¹ and Y², n is independently an integer of 1-4
for each repeating unit of [A-X—Z]$_n$, when (CR¹R²)$_k$ is present, k is independently an integer of 1-4
p and q are independently 1-4
G$_m^1$ and G$_m^2$ are independently absent, or selected independently of each other and, when present, each repeating subunit is independently selected from H, oxoacid, polyethylene glycol having from 2 to 5 ethylene oxide units, or a vitamin compound;
where m is selected independently for G¹ and G², and is an integer of 1-4, except that m is 1 when G¹ or G² is a hydrogen atom;
or a pharmaceutically acceptable salt thereof.

7. The compound or composition of Paragraph 6, wherein L¹ and Y¹ are absent, G¹ is at least one oxoacid and m is 1-3 and wherein M is —(CR³R⁴)$_q$—; W, L² and Y² are absent; G² is at least one oxoacid; and m is 1-3.

8. The compound or composition of any one of Paragraphs 1-7, wherein the at least one oxoacid is at least one carboxylic acid.

9. The compound or composition of any of Paragraphs 1-7, wherein the at least one oxoacid is at least one amino acid.

10. The compound or composition of any one of Paragraphs 1-7, wherein the at least one oxoacid is a combination of at least one carboxylic acid and at least one amino acid.

11. The compound or composition of Paragraph 8 or 10, wherein the carboxylic acid is selected from the group consisting of aliphatic carboxylic acid, aryl carboxylic acid, dicarboxylic acid, and polycarboxylic acid.

12. The compound or composition of Paragraph 11, wherein the carboxylic acid is an aliphatic carboxylic acid selected from the group consisting of saturated carboxylic acids, monounsaturated carboxylic acids, polyunsaturated carboxylic acids, acetylenic carboxylic acids, substituted carboxylic acids, heteroatom containing carboxylic acids and ring containing carboxylic acids.

13. The compound or composition of Paragraph 12, wherein the saturated carboxylic acid is selected from the group consisting of methanoic, ethanoic, propanoic, butanoic, pentanoic, hexanoic, heptanoic, octanoic, 2-propylpentanoic acid, pivalic acid, nonanoic, decanoic, dodecanoic, tetradecanoic, hexadecanoic, heptadecanoic, octadecanoic, and eicosanoic acid.

14. The compound or composition of Paragraph 12, wherein the monounsaturated carboxylic acid is selected from the group consisting of 4-decenoic, 9-decenoic, 5-lauroleic, 4-dodecenoic, 9-tetradecenoic, 5-tetradecenoic, 4-tetradecenoic, 9-hexadecenoic, 6-hexadecenoic, 6-octadecenoic, and 9-octadecenoic acid.

15. The compound or composition of Paragraph 12, wherein the polyunsaturated carboxylic acid is selected from the group consisting of sorbic, octadecadienoic, octadecatrienoic, octadecatetraenoic, eicosatrienoic, eicosatetraenoic, eicosapentaenoic, docosapentaenoic, and docosahexaenoic acids.

16. The compound or composition of Paragraph 12, wherein the acetylenic carboxylic acid is selected from the group consisting of octadecynoic, octadecenynoic, 6,9-octadecenynoic, heptadecenynoic, tridecatetraenediynoic, tridecadienetriynoic, octadecadienediynoic, heptadecadienediynoic, octadecadienediynoic, octadecenediynoic, and octadecenetriynoic acids.

17. The compound or composition of Paragraph 12, wherein the substituted carboxylic acid is selected from the group consisting of methylpropanoic, isovaleric, methylhexadecanoic, 8-methyl-6-nonenoic, methyloctadecanoic, trimethyloctacosanoic, trimethyltetracosanoic, heptamethyltriacontanoic, tetramethylhexadecanoic, tetramethylpentadecanoic, lactic, glyceric, glycolic, threonic, 3-hydroxypropionic, hydroxyoctadecatrienoic, hydroxyoctadecenoic, hydroxytetracosanoic, 2-hydroxybutyric, 3-hydroxybutyric, 4-hydroxybutyric, 4-hydroxypentanoic, hydroxyoctadecadiynoic, hydroxyoctadecadienoic, 10-hydroxydecanoic, hydroxydecenoic, hydroxyeicosenoic, hydroxyeicosadienoic, hydroxyhexadecanoic, dihydroxytetracosenoic, dihydroxydocosanoic, hydroxydocosanoic, trihydroxyoctadecanoic, trihydroxyhexadecanoic, trihydroxyicosahexaenoic, trihydroxyicosapentaenoic, 2-methoxy-5-hexadecenoic, 2-methoxy hexadecanoic, 7-methoxy-4-tetradecenoic, 9-methoxypentadecanoic, 11-methoxyheptadecanoic, 3-methoxydocosanoic, diacetoxydocosanoic, 2-acetoxydocosanoic, 2-acetoxytetracosanoic, 2-acetoxyhexacosanoic, 9-oxononanoic, oxodecanoic, oxododecenoic, hydroxyoxodecenoic, 10-oxo-8-decenoic, fluorooctadecenoic, fluorodecanoic, fluorotetradecanoic, fluorohexadecanoic, fluorooctadecadienoic, chlorohydroxyhexadecanoic, chlorohydroxyoctadecanoic, dichlorooctadecanoic, 3-bromo-2-nonaenoic, 9,10-dibromooctadecanoic, 9,10,12, 13-tetrabromooctadecanoic, 10-nitro-9,12-octadecadienoic, 12-nitro-9,12-octadecadienoic, 9-nitro-9-octadecenoic, 9-oxo-2-decenoic, 9-oxo-13-octadecenoic, oxooctadecatrienoic, 15-oxo-18-tetracosenoic, 17-oxo-20-hexacosenoic, and 19-oxo-22-octacosenoic acids.

18. The compound or composition of Paragraph 12, wherein the heteroatom containing carboxylic acid is selected from the group consisting of 9-(1,3-nonadienoxy)-

8-nonenoic, 9-(1,3,6-nonatrienoxy)-8-nonenoic, 12-(1-hexenoxy)-9,11-dodecadienoic, 12-(1,3-hexadienoxy)-9,11-dodecadienoic, 2-dodecylsulfanylacetic, 2-tetradecylsulfanylacetic, 3-tetradecylsulfanylprop-2-enoic, and 3-tetradecylsulfanylpropanoic acid.

19. The compound or composition of Paragraph 12, wherein the ring containing carboxylic acid is selected from the group consisting of 10-(2-Hexylcyclopropyl)decanoic, 3-(2-[6-bromo-3,5-nondienylcyclopropyl)propanoic, 9-(2-hexadecylcyclopropylidene)non-5-enoic, 8-(2-octyl-1-cyclopropenyl)octanoic, 7-(2-octyl-1-cyclopropenyl)heptanoic, 9,10-epoxyoctadecanoic, 9,10-epoxy12-octadecenoic, 12,13-epoxy-9-octadecenoic, 14,15-epoxy-11-eicosenoic, 11-(2-cyclopenten-1-yl)undecanoic, 13-(2-cyclopenten-1-yl)tridecanoic, 13-(2-cyclopentenyl)-6-tridecenoic, 11-cyclohexylundecanoic, 13-cyclohexyltridecanoic, 7-(3,4-dimethyl-5-pentylfuran-2-yl)heptanoic, 9-(4-methyl-5-pentylfuran-2-yl)nonanoic, 4-[5]-ladderane-butanoic, 6-[5]-ladderane-hexanoic, and 6-[3]-ladderane-hexanoic acid.

20. The compound or composition of Paragraph 8 or 10, wherein the carboxylic acid is a benzoate or a heteroaryl carboxylic acid.

21. The compound or composition of Paragraph 20, wherein the benzoate is selected from the group consisting of benzoic acid, hydroxybenzoate, and combinations thereof.

22. The compound or composition of Paragraph 21, wherein the hydroxybenzoate is selected from the group consisting of salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflunisal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, and 3,4,5-trimethoxybenzoic acid.

23. The compound or composition of Paragraph 20, wherein the heteroaryl carboxylic acid is selected from the group consisting of nicotinic acid, isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, and 7,8-dihydro-7,8-dihydroxykynurenic acid.

24. The compound or composition of Paragraph 8 or 10, wherein the carboxylic acid is a phenylacetate, a branched phenylpropionate, an unbranched phenylpropionate (benzylacetate), a phenylpropenoate (cinnamate), salts thereof, derivatives thereof, or a combination thereof.

25. The compound or composition of Paragraph 24, wherein the phenylacetate is selected from the group consisting of phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, and naproxen.

26. The compound or composition of Paragraph 24, wherein the carboxylic acid is a benzylacetate selected from the group consisting of benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, and phenylpyruvic acid.

27. The compound or composition of Paragraph 24, wherein the carboxylic acid is a cinnamate, derivatives thereof, or combinations thereof.

28. The compound or composition of Paragraph 27, wherein the cinnamate is selected from the group consisting of cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, and 2-hydroxy-3-phenylpropenoic acid.

29. The compound or composition of Paragraph 11, wherein the dicarboxylic acid is of the general formula HOOC—R—COOH, where R is selected from the group consisting of an alkyl, alkenyl, alkynyl, arylgroup, and derivatives thereof.

30. The compound or composition of Paragraph 29, wherein the dicarboxylic acid is selected from the group consisting of oxalic, malonic, succinic, glutaric, adipic, pimelic, suberic, azelaic, sebacic, brassylic, thapsic, malic, tartaric, dihydroxymesoxalic, Q-hydroxyglutaric, methylmalonic, meglutol, diaminopimelic, carbamoyl aspartic, fumaric, maleic, mesaconic, 3-methylglutaconic, traumatic, phthalic acid, isophthalic, terephthalic, and dipicolinic acid.

31. The compound or composition of Paragraph 11, wherein the polycarboxylic acid is selected from the group consisting of citric acid, isocitric, carballylic, and trimesic acid.

32. The compound or composition of any one of Paragraphs 1 to 7, wherein the oxoacid is an amino acid.

33. The compound or composition of Paragraph 32, wherein the amino acid is selected from standard amino acids, non-standard amino acids, synthetic amino acids, and combinations thereof.

34. The compound or composition of Paragraph 32, wherein the amino acid is a standard amino acid.

35. The compound or composition of Paragraph 32, wherein the amino acid is a non-standard amino acid.

36. The compound or composition of Paragraph 32, wherein the amino acid is a synthetic amino acid.

37. The compound or composition of Paragraph 1, wherein M is —$(CR^3R^4)_q$—, W is —O—, $L^2$ and $Y^2$ are present, A is —$CR^1R^2$—, X is absent, Z is —$CR^1R^2$— or absent, and $G^2$ is polyethylene glycol.

38. The compound or composition of Paragraph 37, wherein the terminal hydroxyl group of the polyethylene glycol is substituted with an amino, azide, or methoxy group.

39. The compound or composition of Paragraph 37 or 38, wherein $R^1$, $R^2$, $R^3$ are H; $R^4$ is H, methyl or phenyl; and q is 1.

40. The compound or composition of Paragraph 1, wherein M is —$(CR^3R^4)_q$—; W, L and Y are absent; and G is a vitamin compound.

41. The compound or composition of Paragraph 40, wherein $R^3$ is H; $R^4$ is H, methyl or phenyl; and q is 1-2.

42. The compound or composition of Paragraph 1, wherein M is —(CR$^3$R$^4$)$_q$—, W is —O—, L$^2$ and Y$^2$ are present, A is O, X and Z are absent, and G$^2$ is a vitamin compound.

43. The compound or composition of Paragraph 42, wherein R$^3$ is H; R$^4$ is H, methyl or phenyl; and q is 1-2.

44. The compound or composition of Paragraph 6, wherein at least one of G$^1$ or G$^2$ is a vitamin compound.

45. The compound or composition of any one of Paragraphs 40, 41, or 44, wherein the vitamin compound is a water soluble vitamin compound selected from biotin, folic acid, niacin, and pantothenic acid.

46. The compound or composition of any one of Paragraphs 42-44, wherein the vitamin compound is a water soluble vitamin compound selected from ascorbic acid, riboflavin, thiamin, pantothenic acid, pyridoxine, pyridoxamine, and pyridoxal.

47. The compound or composition of any one of Paragraphs 42-44, wherein the vitamin compound is a fat soluble vitamin compound.

48. The compound or composition of Paragraph 47, wherein the vitamin compound is selected from retinol, cholecalciferol, ergocalciferol, and tocopherols.

49. The compound or composition of any one of Paragraphs 1-48, wherein the pharmaceutically acceptable salt of the conjugate comprises a pharmaceutically acceptable anionic salt form or salt mixtures thereof.

50. The compound or composition of Paragraph 49, wherein the anionic salt form is selected from the group consisting of acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, i-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, or undecylenate.

51. The compound or composition of any one of Paragraphs 1-50, wherein the conjugate is a neutral conjugate.

52. The compound or composition of any one of Paragraphs 1-50, wherein the conjugate is a free acid.

53. The compound or composition of any one of Paragraphs 1-50, wherein the conjugate is a free base.

54. The compound or composition of any one of Paragraphs 1-53, wherein the at least one conjugate is in a mixture of racemates, wherein the racemate comprises racemorphan.

55. The compound or composition of Paragraph 1, wherein the at least one conjugate of levorphanol comprises N-(acetyl-OCH$_2$)-levorphanolium having the following chemical structure, or a pharmaceutically acceptable salt thereof:

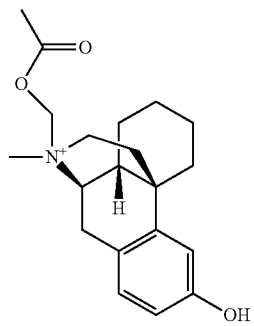 [SMILES: CC(=O)OC[N+]1(C)CC[C@]23CCCC[C@H]2[C@H]1Cc1ccc(O)cc13]

56. The compound or composition of Paragraph 1 wherein the at least one conjugate of levorphanol comprises N-(PheVal-CH$_2$)-levorphanolium having the following structural formula, or a pharmaceutically acceptable salt thereof:

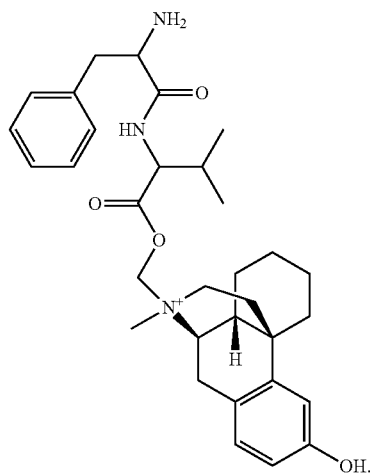 [SMILES: CC(C)C(NC(=O)C(N)Cc1ccccc1)C(=O)OC[N+]1(C)CC[C@]23CCCC[C@H]2[C@H]1Cc1ccc(O)cc13]

57. The compound or composition of Paragraph 1 wherein the at least one conjugate of levorphanol comprises N-(SerIle-CH$_2$)-levorphanolium having the following structural formula, or a pharmaceutically acceptable salt thereof:

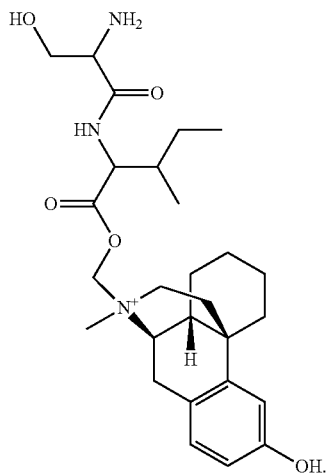 [SMILES: CCC(C)C(NC(=O)C(N)CO)C(=O)OC[N+]1(C)CC[C@]23CCCC[C@H]2[C@H]1Cc1ccc(O)cc13]

58. The compound or composition of Paragraph 1 wherein the at least one conjugate of levorphanol comprises N-(Val- CH$_2$)-levorphanolium having the following structural formula, or a pharmaceutically acceptable salt thereof:

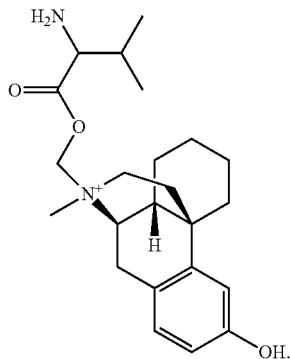 [SMILES: CC(C)C(N)C(=O)OC[N+]1(C)CC[C@]23CCCC[C@H]2[C@H]1Cc1ccc(O)cc13]

59. The compound or composition of Paragraph 1 wherein the at least one conjugate of levorphanol comprises N-(MeO-PEG$_3$-CH$_2$C(O)OCH$_2$)-levorphanolium having the following structural formula, or a pharmaceutically acceptable salt thereof:

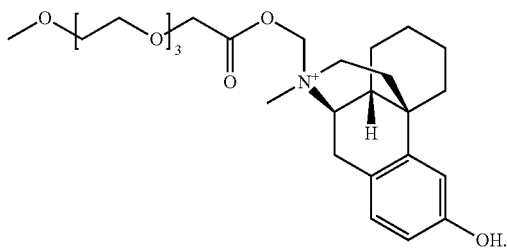

60. The compound or composition of Paragraph 1 wherein the at least one conjugate of levorphanol comprises N-(HO-PEG$_4$-CH$_2$CH$_2$C(O)CH$_2$)-levorphanolium having the following structural formula, or a pharmaceutically acceptable salt thereof:

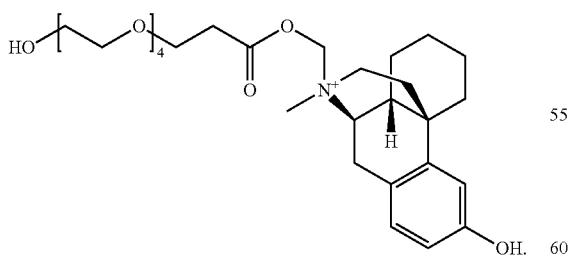

61. The compound or composition of Paragraph 1 wherein the at least one conjugate of levorphanol comprises N-(BzO-CH$_2$OC(O)OCH$_2$)-levorphanolium having the following structural formula, or a pharmaceutically acceptable salt thereof:

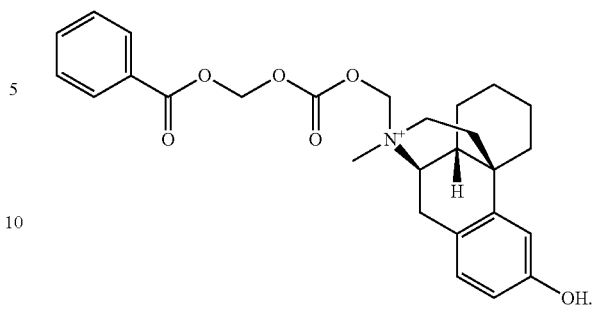

62. The compound or composition of Paragraph 1 wherein the at least one conjugate of levorphanol comprises N-(Ala-CH$_2$OC(O)OCH$_2$)-levorphanolium having the following structural formula, or a pharmaceutically acceptable salt thereof:

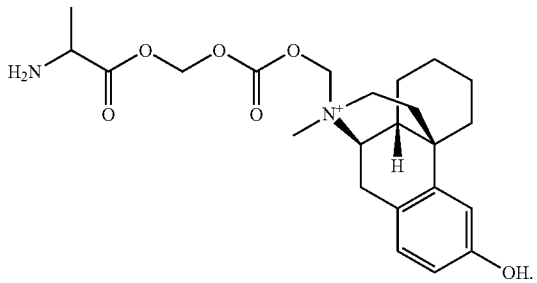 [SMILES: CC(N)C(=O)OCOC(=O)OC[N+]1(C)CC[C@]23CCCC[C@H]2[C@H]1Cc1ccc(O)cc13]

63. The compound or composition of Paragraph 1 wherein the at least one conjugate of levorphanol comprises N-(ProVal-CH$_2$OC(O)OCH$_2$)-levorphanolium having the following structural formula, or a pharmaceutically acceptable salt thereof:

64. The compound or composition of Paragraph 1 wherein the at least one conjugate of levorphanol comprises N-(thiaminyl-C(O)OCH$_2$)-levorphanolium having the following structural formula, or a pharmaceutically acceptable salt thereof:

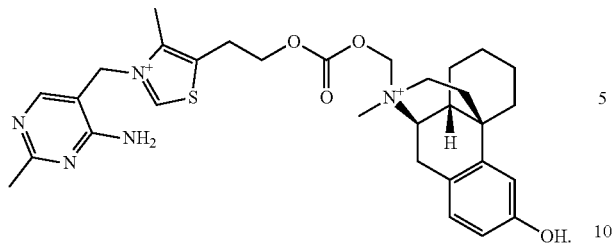

65. The compound or composition of Paragraph 1 wherein the at least one conjugate of levorphanol comprises N-(cinnamoyl-OCH$_2$SC(O)SCH$_2$)-levorphanolium having the following structural formula, or a pharmaceutically acceptable salt thereof:

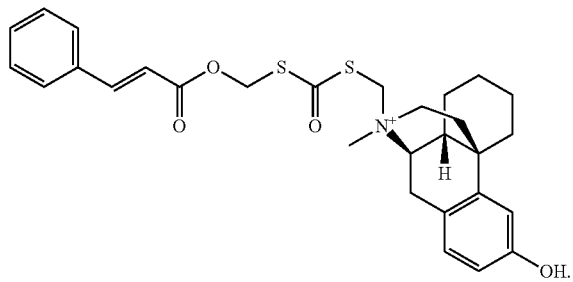 [SMILES: C[N+]1(CSC(=O)SCOC(=O)/C=C/c2ccccc2)CC[C@]23CCCC[C@H]2[C@H]1Cc1ccc(O)cc13]

66. The compound or composition of Paragraph 6, wherein the at least one conjugate of levorphanol comprises 3-acetyl-N-(acetyl-OCH$_2$)-levorphanolium having the following structural formula, or a pharmaceutically acceptable salt thereof:

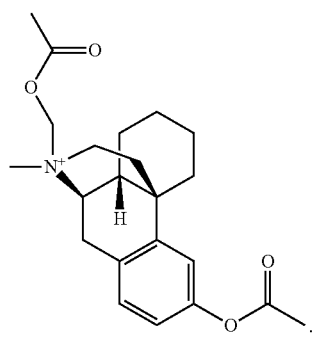 [SMILES: CC(=O)OC[N+]1(C)CC[C@]23CCCC[C@H]2[C@H]1Cc1ccc(OC(C)=O)cc13]

67. The compound or composition of Paragraph 6, wherein the at least one conjugate of levorphanol comprises 3-(pivaloyl)-N-(pivaloyl-OCH$_2$)-levorphanolium having the following structural formula, or a pharmaceutically acceptable salt thereof:

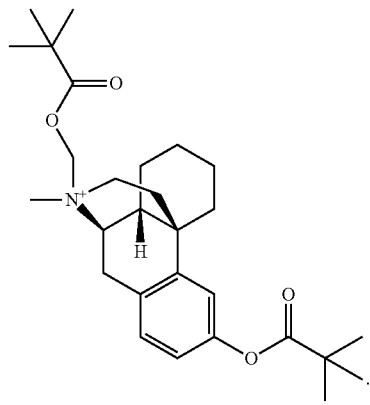 [SMILES: CC(C)(C)C(=O)OC[N+]1(C)CC[C@]23CCCC[C@H]2[C@H]1Cc1ccc(OC(=O)C(C)(C)C)cc13]

68. The compound or composition of Paragraph 6, wherein the at least one conjugate of levorphanol comprises 3-(ethoxy-C(O))—N-(ethoxy-C(O)OCH(CH$_3$))-levorphanolium having the following structural formula, or a pharmaceutically acceptable salt thereof:

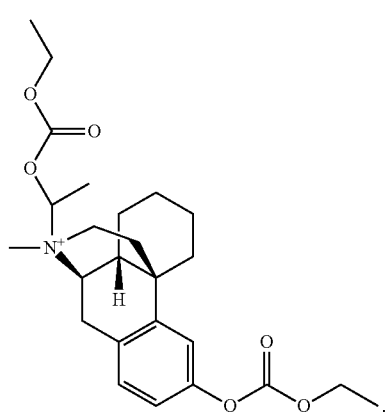 [SMILES: CCOC(=O)Oc1ccc2c(c1)[C@@]13CCCC[C@H]1[C@@H](C2)[N+](C)(C(C)OC(=O)OCC)CC3]

69. The compound or composition of Paragraph 6, wherein the at least one conjugate of levorphanol comprises 3-(EtO—C(O))—N—(H$_2$N-PEG$_2$-CH$_2$CH$_2$C(O)OCH$_2$)-levorphanolium having the following structural formula, or a pharmaceutically acceptable salt thereof:

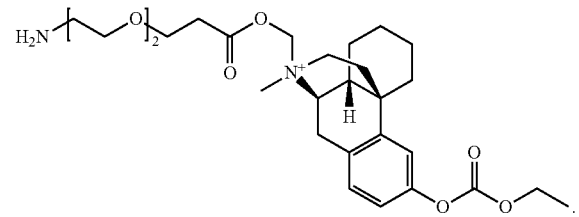

70. The compound or composition of Paragraph 6, wherein the at least one conjugate of levorphanol comprises 3-(Ac-Val)-N-(PhePheCH$_2$)-levorphanolium having the following structural formula, or a pharmaceutically acceptable salt thereof:

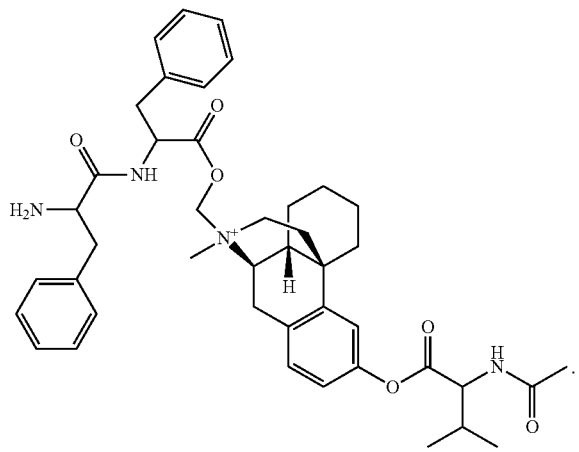 [SMILES: CC(=O)NC(C(=O)Oc1ccc2c(c1)[C@@]13CCCC[C@H]1[C@@H](C2)[N+](C)(COC(=O)C(Cc1ccccc1)NC(=O)C(N)Cc1ccccc1)CC3)C(C)C]

71. The compound or composition of Paragraph 6, wherein the at least one conjugate of levorphanol comprises 3-(acetylsalicyloyl-OCH$_2$OC(O))—N-(Ac-Val-CH$_2$)-levorphanolium having the following structural formula, or a pharmaceutically acceptable salt thereof:

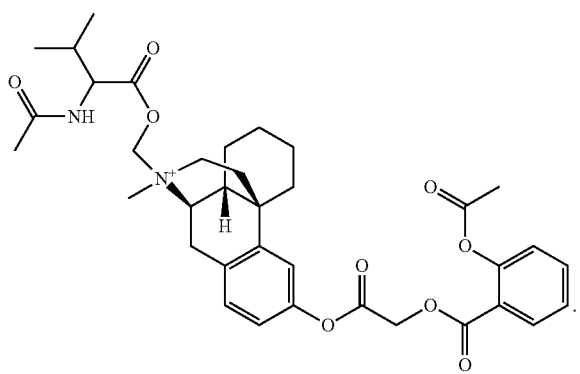 [SMILES: CC(=O)NC(C(=O)OC[N+]1(C)CC[C@]23CCCC[C@H]2[C@H]1Cc1ccc(OC(=O)COC(=O)c2ccccc2OC(C)=O)cc13)C(C)C]

72. The compound or composition of Paragraph 6, wherein the at least one conjugate of levorphanol comprises 3-(Phe-CH(Me)C(O))—N-(nicotinoyl-OCH$_2$)-levorphanolium having the following structural formula, or a pharmaceutically acceptable salt thereof:

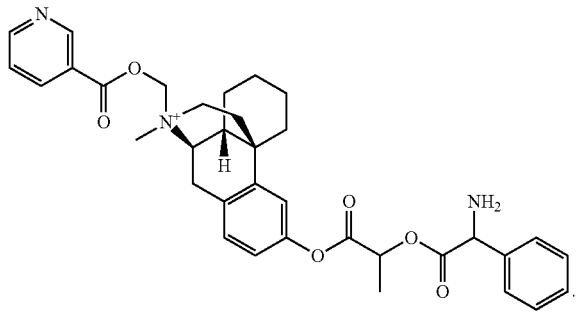 [SMILES: CC(OC(=O)C(N)c1ccccc1)C(=O)Oc1ccc2c(c1)[C@@]13CCCC[C@H]1[C@@H](C2)[N+](C)(COC(=O)c1cccnc1)CC3]

73. The compound or composition of any one of paragraphs 1-72, wherein the at least one conjugate is present in an amount of about 0.5 mg or higher, about 2.5 mg or higher, about 5 mg or higher, about 10 mg or higher, about 20 mg or higher, about 50 mg or higher, or about 100 mg or higher.

74. The compound or composition of any one of paragraphs 1-73, wherein the at least one conjugate is provided in a dosage form selected from the group consisting of: a tablet, a capsule, a caplet, a suppository, a troche, a lozenge, an oral powder, a solution, a syrup, an oral film, a thin strip, a slurry, and a suspension.

75. The compound or composition of any one of paragraphs 1-74, wherein the at least one conjugate exhibits a slower rate of release over time as compared to unmodified levorphanol.

76. The composition of any one of paragraphs 1-75, wherein the composition further comprises one or more excipients.

77. The composition of paragraph 76, wherein the one or more excipients is at least one filler, at least one glidant, at least one binder, at least one diluent, at least one lubricant, at least one surfactant, at least one plasticizer, at least one disintegrant, or a combination thereof.

78. The composition of any one of paragraphs 1-77, wherein the composition further comprises at least one additional active pharmaceutical ingredient.

79. The composition of paragraph 78, wherein the additional active pharmaceutical ingredient is hydromorphone, hydrocodone, oxycodone, oxymorphone, conjugates thereof, or combinations thereof.

80. The composition of paragraph 78, wherein the additional active pharmaceutical ingredient is in the form of a second conjugate.

81. The composition of paragraph 80, wherein the second conjugate is a levorphanol conjugate that is different from the at least one conjugate.

82. The composition of paragraph 80, wherein the second conjugate is a dextrorphan conjugate 83. A method of treating a patient having pain, comprising orally administering to the patient a pharmaceutically effective amount of a composition comprising at least one conjugate of levorphanol and at least one oxoacid, polyethylene glycol, vitamin compound, or a combination thereof.

84. The method of paragraph 83, wherein the patient is a pediatric patient, an adolescent patient, an elderly patient, a normative patient, or a neonatal patient.

85. A pharmaceutical kit comprising:
   a specified amount of individual doses in a package, wherein each dose comprises a pharmaceutically effective amount of at least one conjugate of levorphanol and at least one oxoacid, polyethylene glycol, vitamin compound, or a combination thereof.

86. The pharmaceutical kit of paragraph 85, wherein the kit further comprises: instructions for use of the kit in a method for treating pain in a human or animal patient.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

What is claimed is:
1. A compound of Formula 1:

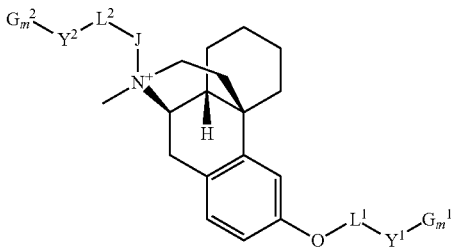

where $L^1$ and $L^2$ are independently absent, or

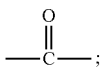

$Y^1$ and $Y^2$ are independently either absent, or $[A-X-Z]_n$ where A, X, Z are independently selected for $Y^1$ and $Y^2$ and where A and Z are independent of each other, either absent or selected from the group of —O—, —S—, or —$(CR^1R^2)_k$—, where X is —$(CR^1R^2)_k$—, J is [M-W]p where M is —$(CR^3R^4)_q$—; and W is absent, or —O— or —S—

$R^1$, and $R^2$, are each independently selected for $Y^1$ and $Y^2$, and are, independent of each other, selected from H, alkyl, aryl, alkyl aryl, alkoxy, haloalkyl, or haloaryl $R^3$ and $R^4$ are each independently selected from H, alkyl, aryl, alkyl aryl, alkoxy, haloalkyl, or haloaryl for each $Y^1$ and $Y^2$, n is independently an integer of 1-4 for each repeating unit of $[A-X-Z]_n$, when $(CR^1R^2)$ is present, k is independently an integer of 1-4 p and q are independently selected from 1-4

$G_m$ is absent, or selected independently of each other and, when present, each repeating subunit is independently selected from H, oxoacid, polyethylene glycol having from 2 to 5 ethylene oxide units, or a vitamin compound;

$G_m^2$ is selected from oxoacid, polyethylene glycol having from 2 to 5 ethylene oxide units, or a vitamin compound;

where m is selected independently for $G^1$ and $G^2$, and is an integer of 1-4, except that m is 1 when $G^1$ is a hydrogen atom;

or a pharmaceutically acceptable salt thereof.

2. The compound of claim 1, wherein $L^1$ and $Y^1$ are absent, $G^1$ is at least one oxoacid and m is 1-3 and wherein M is —$(CR^3R^4)_q$—; W, $L^2$ and $Y^2$ are absent; $G^2$ is at least one oxoacid; and m is 1-3.

3. The compound of claim 1, wherein the oxoacid is at least one amino acid, is at least one carboxylic acid, or is a combination of at least one carboxylic acid and at least one amino acid.

4. The compound of claim 3, wherein the at least one carboxylic acid is selected from the group consisting of aliphatic carboxylic acid, aryl carboxylic acid, dicarboxylic acid, polycarboxylic acid, benzoate, phenylacetate, a branched phenylpropionate, an unbranched phenylpropionate (benzylacetate), a phenylpropenoate (cinnamate), and heteroaryl carboxylic acid, salts thereof or a combination thereof.

5. The compound of claim 4, wherein the benzoate is selected from the group consisting of benzoic acid, hydroxybenzoate, and combinations thereof.

6. The compound of claim 5, wherein the hydroxybenzoate is selected from the group consisting of salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflunisal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, and 3,4,5-trimethoxybenzoic acid.

7. The compound of claim 4, wherein the heteroaryl carboxylic acid is selected from the group consisting of nicotinic acid, isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, and 7,8-dihydro-7,8-dihydroxykynurenic acid.

8. The compound of claim 4, wherein the phenylpropenoate (cinnamate) is selected from the group consisting of cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, and 2-hydroxy-3-phenylpropenoic acid.

9. The compound of claim 3 wherein the at least one amino acid is a standard amino acid.

10. The compound of claim 1, wherein the compound is a neutral conjugate, a free acid, a free base or a mixture of racemates, wherein the racemate comprises racemorphan.

11. A composition comprising the compound of claim 1 or a pharmaceutically acceptable salt of the compound.

12. The composition of claim 11, wherein the pharmaceutically acceptable salt is selected from the group consisting of acetate, 1-aspartate, besylate, bicarbonate, carbonate, d-camsylate, 1-camsylate, citrate, edisylate, formate, fumarate, gluconate, hydrobromide/bromide, hydrochloride/chloride, d-lactate, i-lactate, d,l-lactate, d,l-malate, 1-malate, mesylate, pamoate, phosphate, succinate, sulfate, bisulfate, d-tartrate, 1-tartrate, d,l-tartrate, meso-tartrate, benzoate, gluceptate, d-glucuronate, hybenzate, isethionate, malonate, methylsulfate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, undecylenate or combinations thereof.

13. The composition of claim 11, wherein the compound is present in an amount of about 0.5 mg or higher.

14. The composition of claim 11, wherein the compound is provided in a dosage form selected from the group consisting of a tablet, a capsule, a caplet, a suppository, a troche, a lozenge, an oral powder, a solution, an oral film, a thin strip, a slurry, a suspension, and a transdermal patch.

15. The composition of claim 11, wherein the composition further comprises at least one additional active pharmaceutical ingredient.

* * * * *